United States Patent
Derr

(10) Patent No.: US 8,083,354 B2
(45) Date of Patent: Dec. 27, 2011

(54) SIMULTANEOUSLY MULTI-TEMPORAL VISUAL TEST AND METHOD AND APPARATUS THEREFOR

(75) Inventor: Peter H. Derr, East Windsor, NJ (US)

(73) Assignee: Diopsys, Inc., Pine Brook, NJ (US)

( * ) Notice: Subject to any disclaimer, the term of this patent is extended or adjusted under 35 U.S.C. 154(b) by 495 days.

(21) Appl. No.: 11/905,698

(22) Filed: Oct. 3, 2007

(65) Prior Publication Data

US 2009/0091706 A1    Apr. 9, 2009

(51) Int. Cl.
*A61B 3/02* (2006.01)
*A61B 3/00* (2006.01)

(52) U.S. Cl. .................................. 351/246; 351/239

(58) Field of Classification Search .................. 351/200, 351/205, 206, 239, 246
See application file for complete search history.

(56) References Cited

U.S. PATENT DOCUMENTS

| | | | |
|---|---|---|---|
| 5,539,482 A | 7/1996 | James et al. | |
| 6,315,414 B1* | 11/2001 | Maddess et al. | 351/246 |
| 6,475,162 B1 | 11/2002 | Hu | |
| 6,477,407 B1 | 11/2002 | Klistorner et al. | |
| 6,527,391 B1 | 3/2003 | Heijl et al. | |
| 6,688,746 B2 | 2/2004 | Malov | |
| 6,840,622 B2 | 1/2005 | Kutschbach et al. | |
| 6,966,650 B2 | 11/2005 | Hu et al. | |
| 7,006,863 B2 | 2/2006 | Maddess et al. | |

* cited by examiner

*Primary Examiner* — Ricky Mack
*Assistant Examiner* — Mahidere Sahle
(74) *Attorney, Agent, or Firm* — Levisohn Berger, LLP

(57) ABSTRACT

A method for determining a likelihood of a visual deficit in a subject uses a simultaneously multi-temporal visual test. At least two visual patterns are simultaneously displayed to the subject. Each pattern reverses in contrast or color at a different display frequency, and each pattern is displayed to a different region of the subject's visual field. Electrical activity of the brain of the subject is captured and sampled, and one or more frequency components are resolved from the resulting signal, where each frequency component corresponds to a different display frequency. The method then involves determining from the frequency components, optionally by comparison between the eyes, a measurement of a likelihood that a visual deficit exists in a particular area.

23 Claims, 28 Drawing Sheets

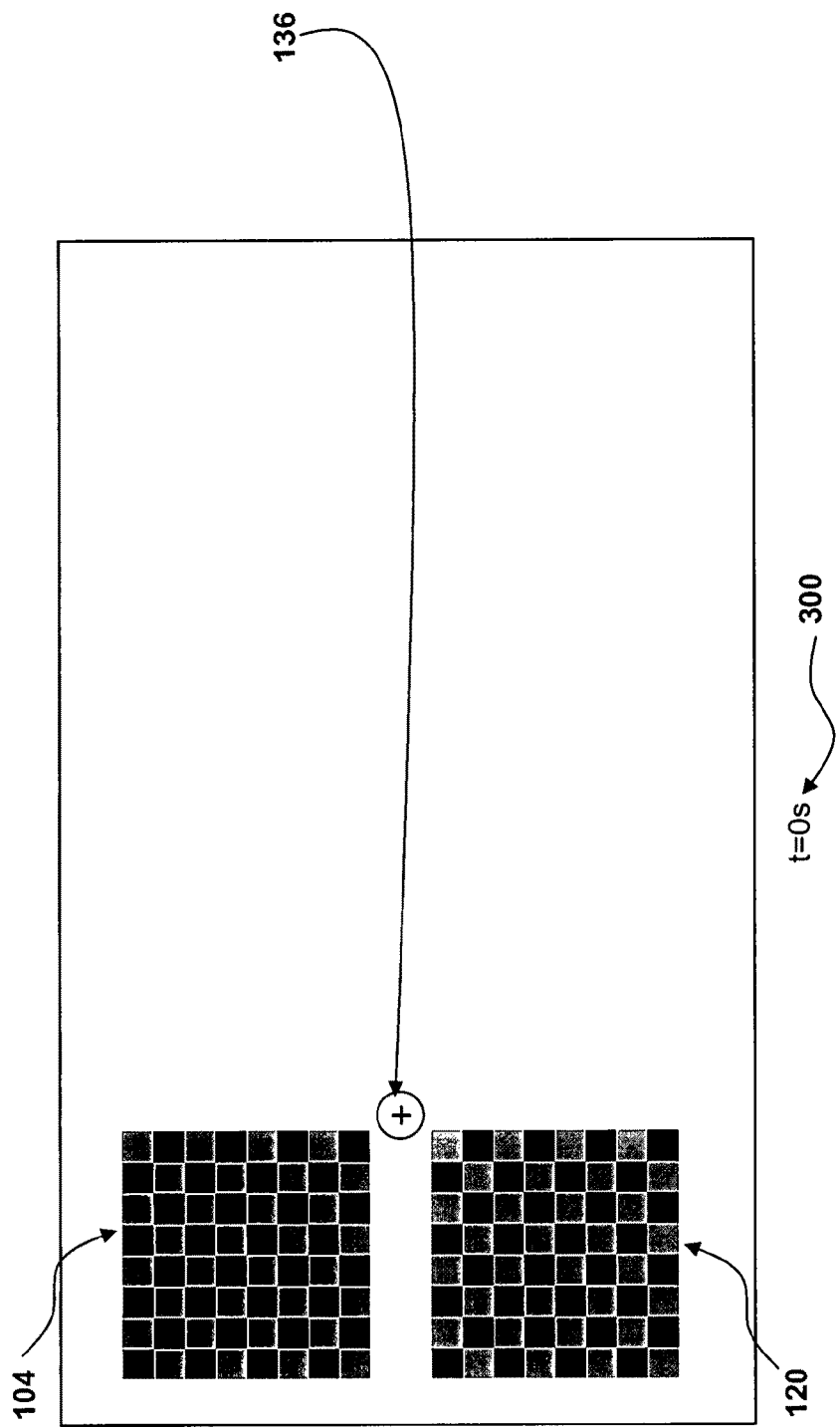

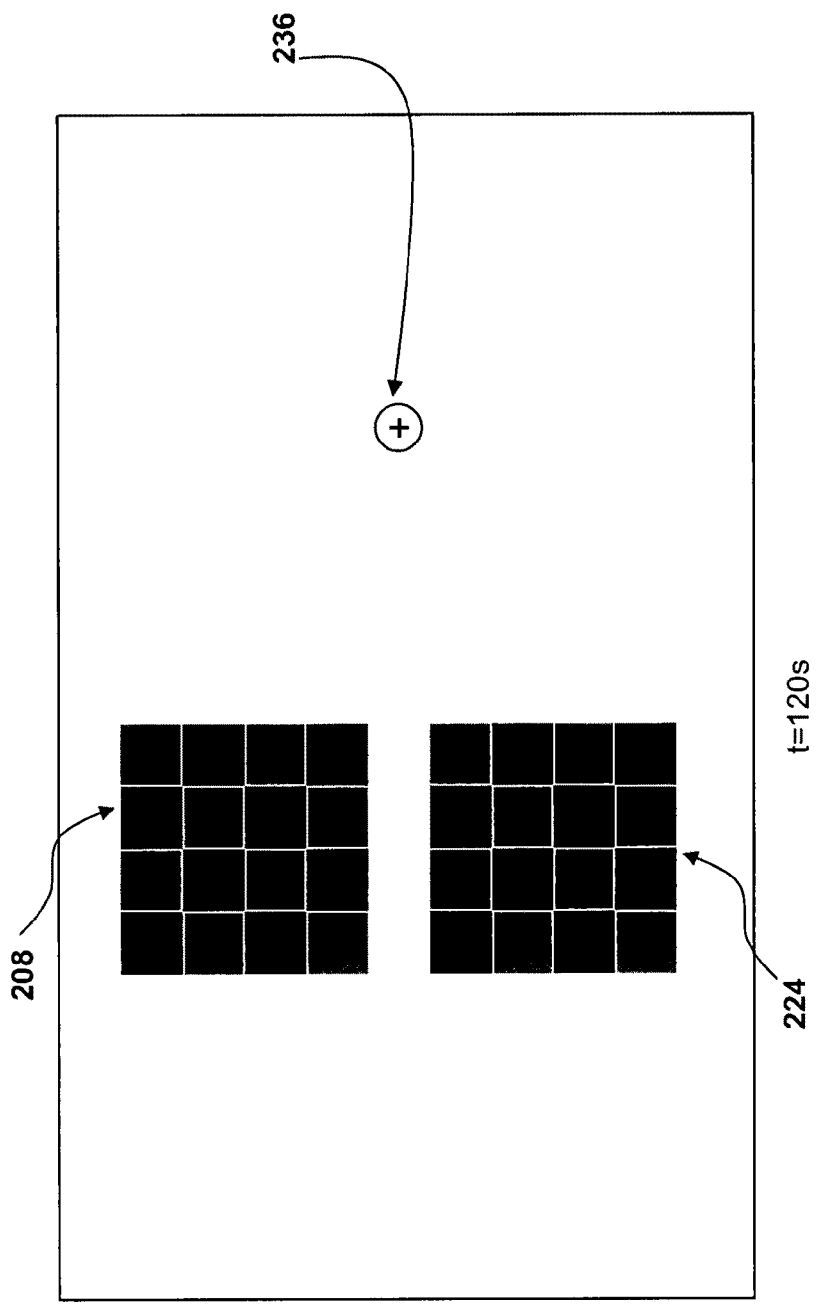

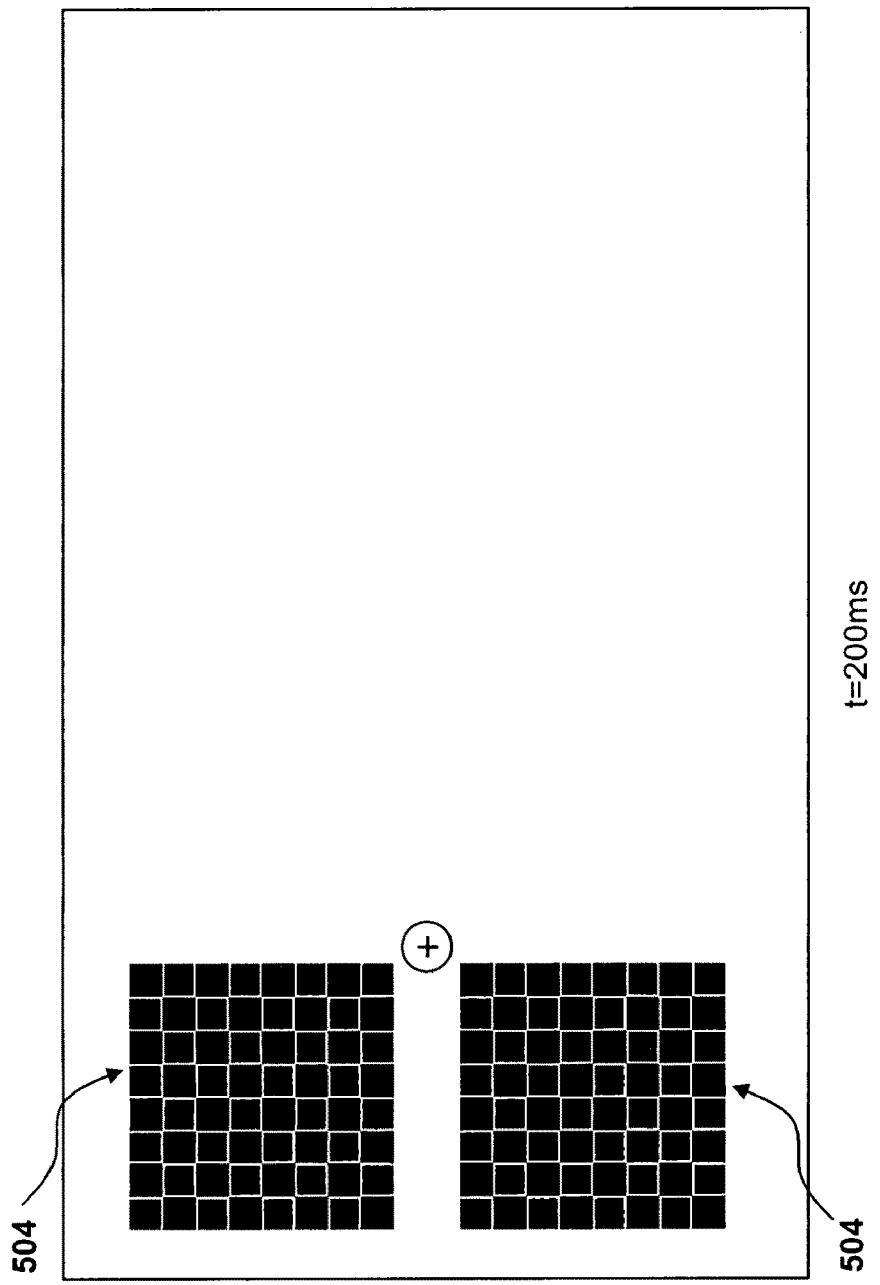

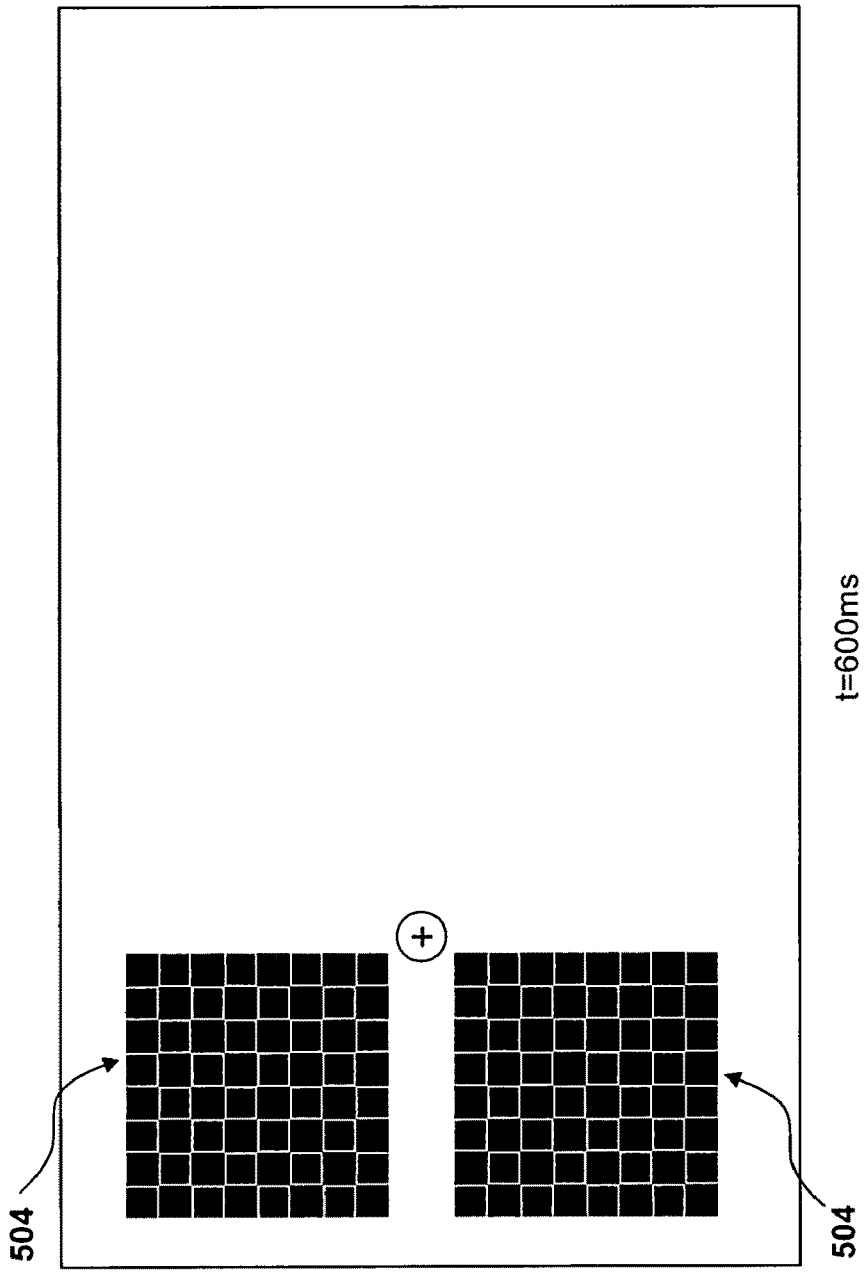

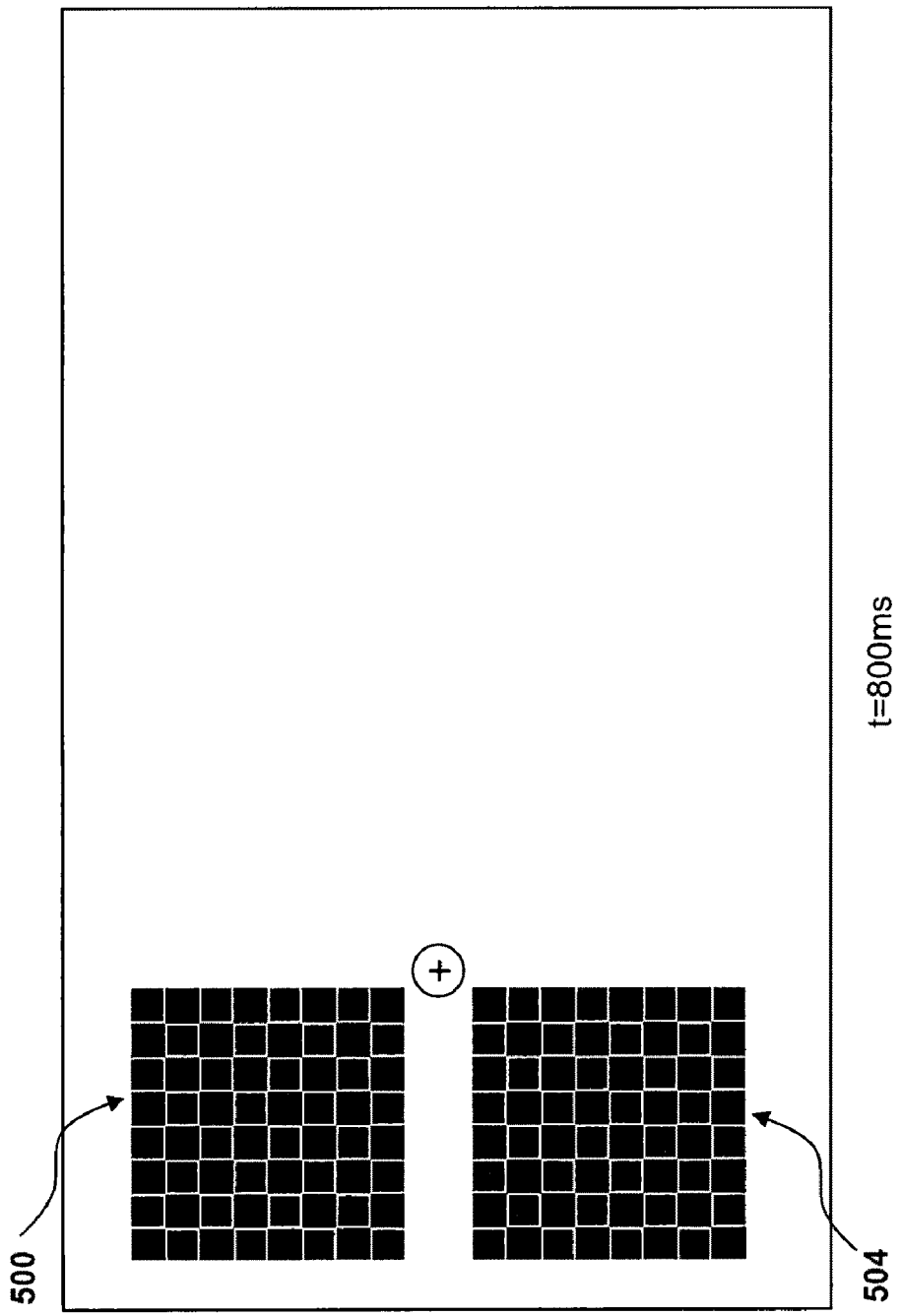

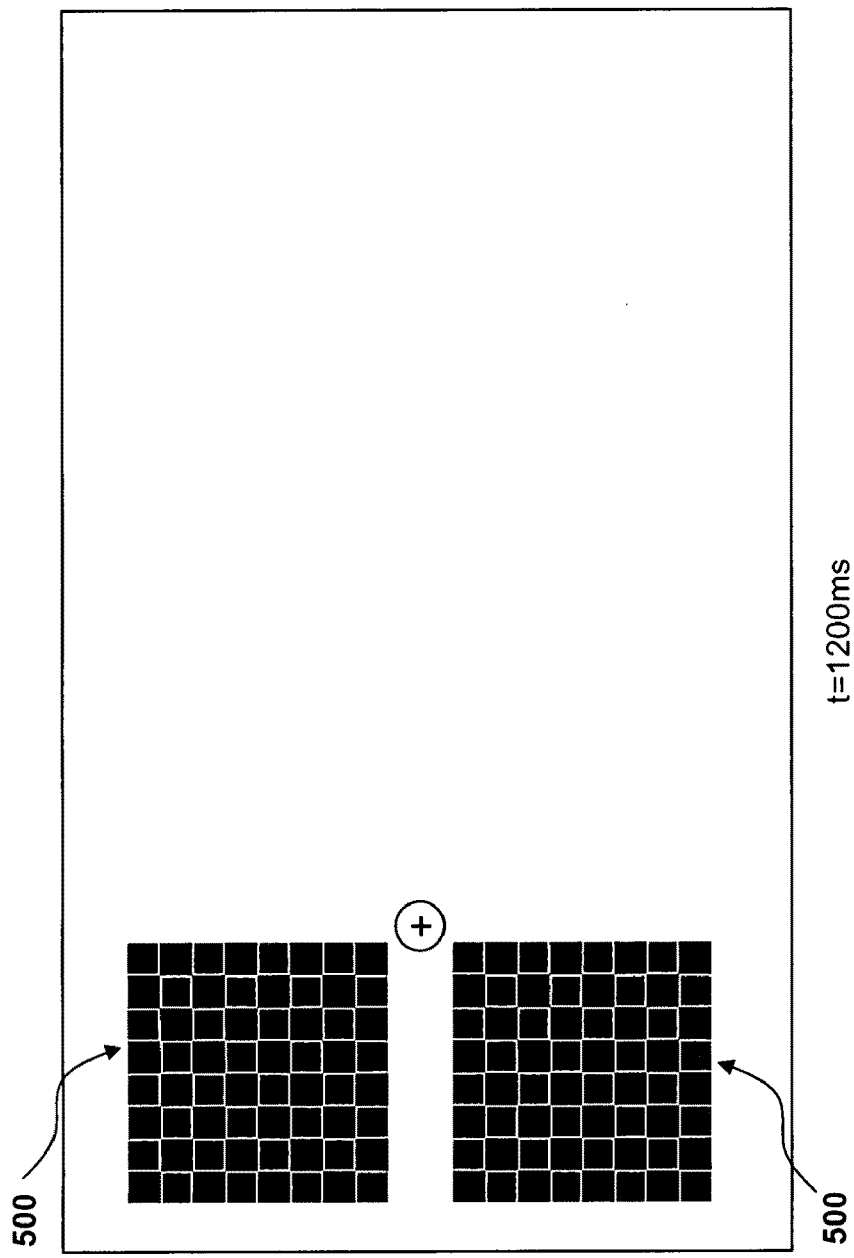

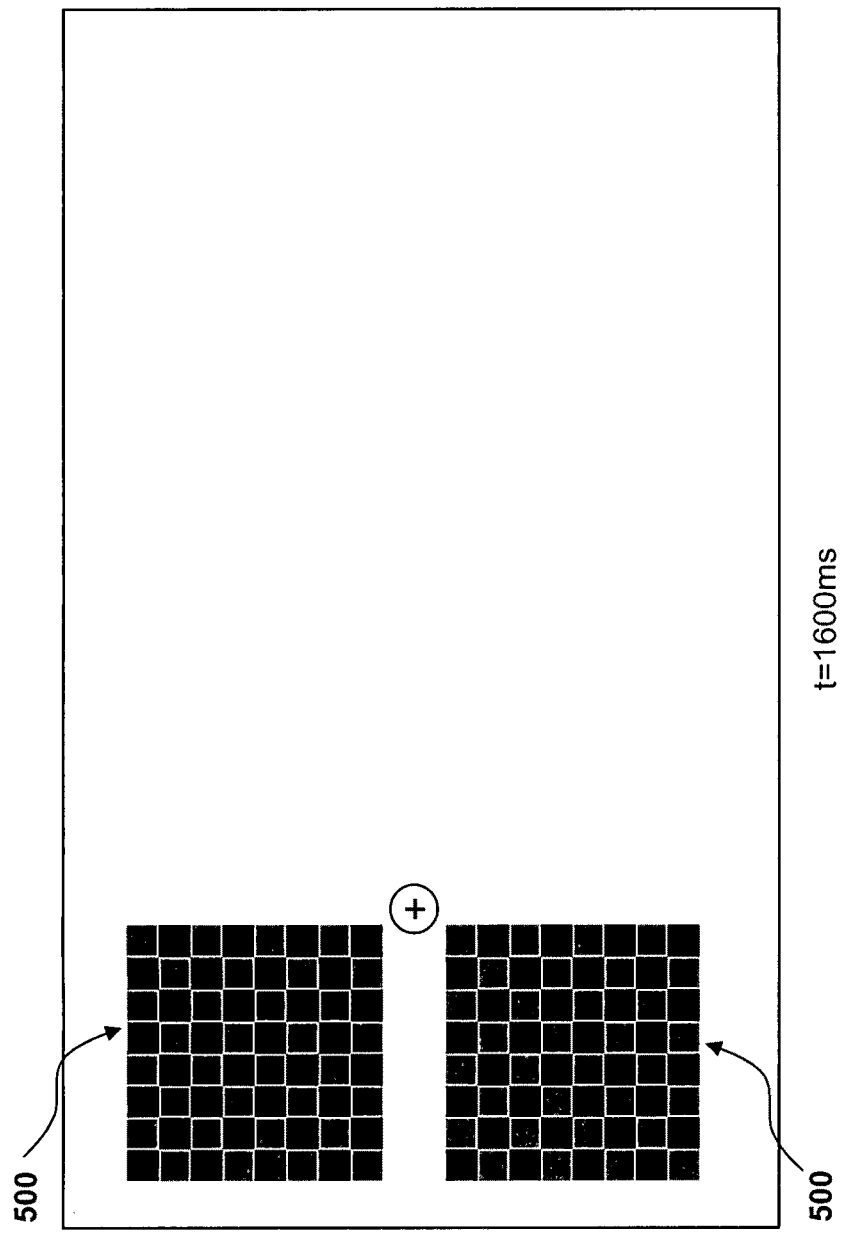

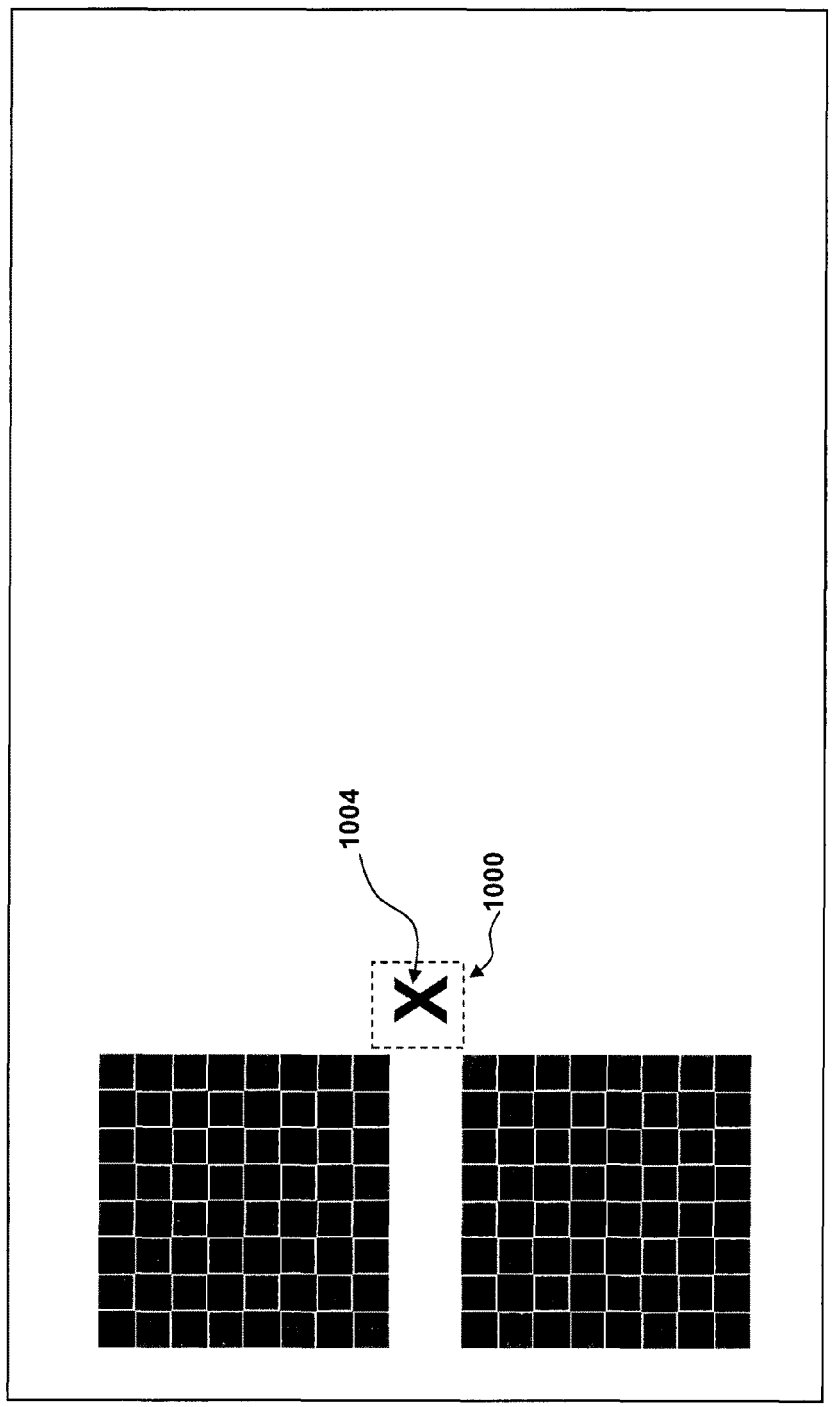

SIMULTANEOUSLY MULTI-TEMPORAL VISUAL TEST AND METHOD AND APPARATUS THEREFOR

BACKGROUND OF THE INVENTION

1. Field of the Invention

The present application relates to methods and apparatuses for performing visual tests, and in particular, methods and apparatuses for performing a simultaneously multi-temporal visual test to determine a likelihood of a visual deficit in a subject.

2. Related Art

A number of methods, apparatuses, and display patterns have been proposed for performing visual tests of a subject, but none disclose the presently claimed methods and apparatuses for performing a simultaneously multi-temporal visual test to determine a likelihood of a visual deficit.

U.S. Pat. No. 6,527,391 to Heijl et al. is drawn to a typical method and apparatus for performing a computerized visual field test for identifying visual deficits. Such visual field tests typically are performed in one region of the eye at a time. They require long testing times, and are compromised when a subject fixates on the wrong portion of a display. The recording of overt responses is also problematic in certain populations, including the prelingual, the nonlingual, the elderly, and those who might intentionally or inadvertently hide their deficits.

U.S. Pat. No. 5,539,482 to James et al. is drawn to a glaucoma test using a pattern electroretinogram of a subject. The visual stimulus signals used are grating patterns, with the contrast of the signal applied to each zone modulated with a different temporal frequency. Differences between electroretinogram components for an individual zone and the expected response component for that zone indicate a change in ganglion cell function in that zone.

The use of an electroretinogram such as that proposed by James et al. for a glaucoma or vision test leads to a number of problems which are overcome by the present disclosure. An electroretinogram is highly problematic, as it requires the attachment of an electrode to the cornea or sclera of a subject, who must thus be sedated or anesthetized for the test. This limits the use of such a test to healthy populations, and demands that the test be performed in sterile environments such as hospitals. Moreover, known variations between subjects may cause the absolute comparison of any electroretinogram component to an "expected response component," as described by James et al., to be inaccurate or insufficiently sensitive. A still further problem is that the electroretinogram only identifies deficits in the retina, and not in all the various other regions of the visual field, such as along the optic pathway or even in the brain.

U.S. Pat. No. 6,840,622 to Kutschbach et al. also discloses the use of an electroretinogram for determining the topography of reaction signals in the eye, and is highly problematic for all of the above reasons.

U.S. Pat. No. 6,477,407 to Klistorner et al. is drawn to the use of a multifocal pattern visual evoked potential (VEP) for use in detecting visual field loss. However, this patent does not disclose, teach, or suggest a simultaneously multi-temporal visual display. This patent is also drawn to the identification of visual field loss by comparing electrical brain activity acquired over two or more regions of the brain, and not by comparing components of VEPs acquired with as little as one electrode pair. The uses of phase, frequency, and magnitude components, compared to each other and to corresponding display factors, are also not disclosed.

U.S. Pat. No. 6,688,746 to Malov is drawn to a method of providing a visual reaction map of at least part of the visual eye field of a subject. However, this patent does not disclose, teach, or suggest comparing components of VEPs acquired with as little as one electrode pair. The uses of phase, frequency, and magnitude components, compared to each other and to corresponding display factors, are also not disclosed.

U.S. Pat. No. 7,006,863 to Maddess is drawn to a method and apparatus which use sparse stimuli to assess neural function. Temporal sequences of stimulus conditions are presented infrequently against a frequent baseline null stimulus condition. However, this patent does not disclose, teach, or suggest a simultaneously multi-temporal visual display, nor does it disclose, teach, or suggest comparing components of VEPs. The uses of phase, frequency, and magnitude components, compared to each other and to corresponding display factors, are also not disclosed.

Thus, there remains a need for a simplified, simultaneously multi-temporal visual test that readily determines the likelihood of a visual deficit in a subject.

SUMMARY OF THE INVENTION

The present subject matter addresses the above concerns by teaching the following methods and apparatuses.

The present disclosure includes a method for determining a likelihood of a visual deficit in a subject by way of a simultaneously multi-temporal visual test. At least two visual patterns are simultaneously displayed to the subject. Each pattern reverses in contrast or color at a different one of a corresponding number of display frequencies, and each pattern is displayed to a different region of the subject's visual field. Electrical activity of the brain of the subject is captured and sampled into a signal, and one or more frequency components are resolved from the signal, where each frequency component corresponds to a different display frequency. The method then involves determining, from one or more of the frequency components, a measurement of a likelihood that a visual deficit exists in a visual area corresponding to the visual field area to which a pattern alternating at the one of the display frequencies was displayed.

In some aspects, the magnitude of one of the frequency components is compared to the magnitude of another of the frequency components. In some aspects, the phase of each frequency component is compared to the phase of the corresponding visual pattern display. In some aspects, a magnitude measurement is taken for each frequency component.

In some aspects, each frequency component corresponding to each of the display frequencies is resolved from the electrical brain activity, and a summed magnitude of a first subset of the frequency components is compared to a summed magnitude of a second subset of the frequency components. As a non-limiting example, the first subset may include frequency components corresponding to display frequencies displayed in the superior half of the subject's visual field, and the second subset may include frequency components corresponding to display frequencies displayed in the inferior half of the subject's visual field. As another non-limiting example, the first subset may include frequency components corresponding to display frequencies displayed in a nasal portion of the subject's visual field, and the second subset may include frequency components corresponding to display frequencies displayed in a temporal portion of the subject's visual field.

In some aspects, up to eight visual patterns are simultaneously displayed to one eye of the subject, each pattern reversing in contrast or color at a different display frequency and phase. In these aspects, half of the visual patterns may be displayed to the superior half of subject's visual field and the other half of the visual patterns may be displayed to the inferior half of subject's visual field.

In some aspects, visual patterns with low contrast are displayed at a location over 5 degrees displaced from the subject's fovea. As a non-limiting example, this may be done to test for glaucoma.

In some aspects, visual patterns with high contrast are displayed at a location between 1.5 degrees and 5 degrees displaced from the subject's fovea. As a non-limiting example, this may be done to test for macular degeneration. Other ranges for pattern placement may be used, including as non-limiting examples: between 0.5 degrees and 10 degrees displaced from the subject's fovea; between 1.5 degrees and 8 degrees displaced from the subject's fovea; and between 2 degrees and 7 degrees displaced from the subject's fovea.

In some aspects, visual patterns with low contrast may be displayed at a location between 1.5 degrees and 5 degrees displaced from the subject's fovea. As a non-limiting example, this may be done as a quality control check. Other ranges for pattern placement may be used, including as non-limiting examples: between 0.5 degrees and 10 degrees displaced from the subject's fovea; between 1.5 degrees and 8 degrees displaced from the subject's fovea; and between 2 degrees and 7 degrees displaced from the subject's fovea.

In some aspects, visual patterns with high contrast may be displayed at a location over 5degrees displaced from the subject's fovea. As a non-limiting example, this may be done as a quality control check. Other pattern placements may be used, including as non-limiting examples: over 7 degrees displaced from the subject's fovea; over 8 degrees displaced from the subject's fovea; and, over 10 degrees displaced from the subject's fovea.

In some aspects, checkerboard patterns of a first grid size are displayed at a location between 1.5 degrees and 5 degrees displaced from the subject's fovea, and checkerboard patterns of a second grid size are displayed at a location over 5 degrees displaced from subject's fovea. Other pattern placements may be used, as described herein.

In some aspects, checkerboard patterns are displayed between 1.5 degrees and 5 degrees displaced from subject's fovea, and are reversed in contrast at a display frequency greater than the largest display frequency at which a checkerboard pattern displayed over 5 degrees displaced from subject's fovea reverses in contrast. Other pattern placements may be used, as described above.

In some aspects, a letter, number, shape, or symbol is displayed at a location to which the subject's vision is directed, and the subject is instructed to identify an occurrence of the display of at least one particular letter, number, shape, or symbol, thereby assuring that the subject's vision remains directed to the desired location.

In some aspects, a further frequency component is resolved from the signal corresponding to a likely alpha or beta wave, and the alpha or beta frequency component is correspondingly removed from the signal prior to the determining step.

In some aspects, the displaying step is performed at least once for the subject's first eye and at least once for the subject's second eye. The patterns for the first eye and the patterns for the second eye are shown to mirror-isometric regions of the first and second visual fields. Then, the magnitude of one of the frequency components resolved from the testing of one eye is compared to the magnitude of one of the frequency components resolved from the testing of the other eye, the compared frequency components corresponding in the visual field regions to which they were displayed.

In some aspects, frequency components are resolved by way of a Fourier transform.

In some aspects, electrical brain activity is captured at a scalp region directly above the visual cortex of the brain.

In some aspects, electrical brain activity is recorded.

In some aspects, confidence intervals are determined for the frequency components or for various inter-test or inter-suite variability measurements. These intervals may be determined by way of $T^2_{circ}$ statistics, although many other statistics are known for confidence measurements and may be used, including as a non-limiting example Least Square Error statistics which maximize the $R^2$ coefficient.

In some aspects, the determination of the likelihood of a visual deficit signifies the presence of one or more of the following: glaucoma; macular degeneration; macular dystrophy; retinitis pigmentosa; Laurence-Moon-Bardet-Biedl syndrome; Stargardt's disease; inflammation of the retina; inflammation of the choroid; Serpiginous Choroiditis; cortical blindness; cataracts; basic refractive problems; strabismus; or combinations thereof.

The present disclosure also includes an apparatus for determining a likelihood of a visual deficit in a subject by way of a simultaneously multi-temporal visual test. The apparatus includes a visual display device configured to simultaneously display at least two visual patterns to one eye of the subject. Each pattern reverses in contrast or color at a different one of a corresponding number of display frequencies. Each pattern is displayed to a different region of the subject's visual field. The visual display device subsequently displays a corresponding plurality of visual patterns to the other eye of the subject. One or more electrodes placed over the visual cortex of the subject capture electrical activity of the brain of the subject during display. A digital-to-analog converter digitally samples the electrical brain activity and produces a corresponding digital signal. A processor is configured to resolve from the digital signal by way of a Fourier transform one or more frequency components, each corresponding to a different display frequency. A comparator determines a measurement of a likelihood that a visual deficit exists in a visual area corresponding to a visual field area to which a pattern was displayed.

In some aspects, a synchronizer synchronizes the sampling of the digital-to-analog converter with the display rate of the visual display device by way of interrupt signals.

In some aspects, the processor is configured to resolve the phase of each frequency component, and the comparator is configured to compare the phase of each frequency component to the phase of the corresponding visual pattern display to compute a phase match measurement for each frequency component.

In some aspects, the processor is configured to take a magnitude measurement of one of the frequency components, and to take a magnitude measurement of the other of the frequency components, and the comparator is configured to compare the respective magnitude measurements.

In some aspects, the comparator is configured to compare magnitudes of a first subset of the frequency components to magnitudes of a second subset of the frequency components to determine a likelihood that a visual deficit exists in a visual area corresponding to a visual field area to which a pattern was displayed.

The present disclosure also includes a system for determining a likelihood of a visual deficit in a subject by way of a simultaneously multi-temporal visual test. The system includes means for simultaneously displaying at least two visual patterns to the subject. Each pattern reverses in contrast or color at a different one of a corresponding number of display frequencies, and each pattern is displayed to a different region of the subject's visual field. The system also includes means for resolving one or more frequency components, each corresponding to a different display frequency, from electrical brain activity captured from the brain of the subject. The system also includes means for determining from one or more of the frequency components a measurement of a likelihood that a visual deficit exists in a visual area corresponding to the visual field area to which a pattern alternating at the one of display frequency was displayed.

In some aspects, a machine readable medium comprises instructions for performing a method for determining a likelihood of a visual deficit in a subject by way of a simultaneously multi-temporal visual test.

BRIEF DESCRIPTION OF THE DRAWINGS

The features, nature, and advantages of the presently disclosed methods and apparatuses will become more apparent from the detailed description set forth below when taken in conjunction with the drawings in which like reference characters identify corresponding items throughout and wherein:

FIGS. 3a-3d illustrate an 80-second sequence of displays to be shown to the right eye of a subject comprising visual patterns according to the present disclosure;

FIGS. 4a-4d illustrate an 80-second sequence of displays to be shown to the left eye of a subject comprising visual patterns according to the present disclosure;

FIGS. 5a-5j illustrate a 2-second sequence of displays to be shown to the right eye of a subject comprising visual patterns according to the present disclosure;

FIGS. 10a-10d illustrate various letters and symbols displayed at a display location to which a subject's vision is directed as part a simultaneously multi-temporal visual test for determining a likelihood of a visual deficit in a subject according to the present disclosure.

DETAILED DESCRIPTION

Figure 1:
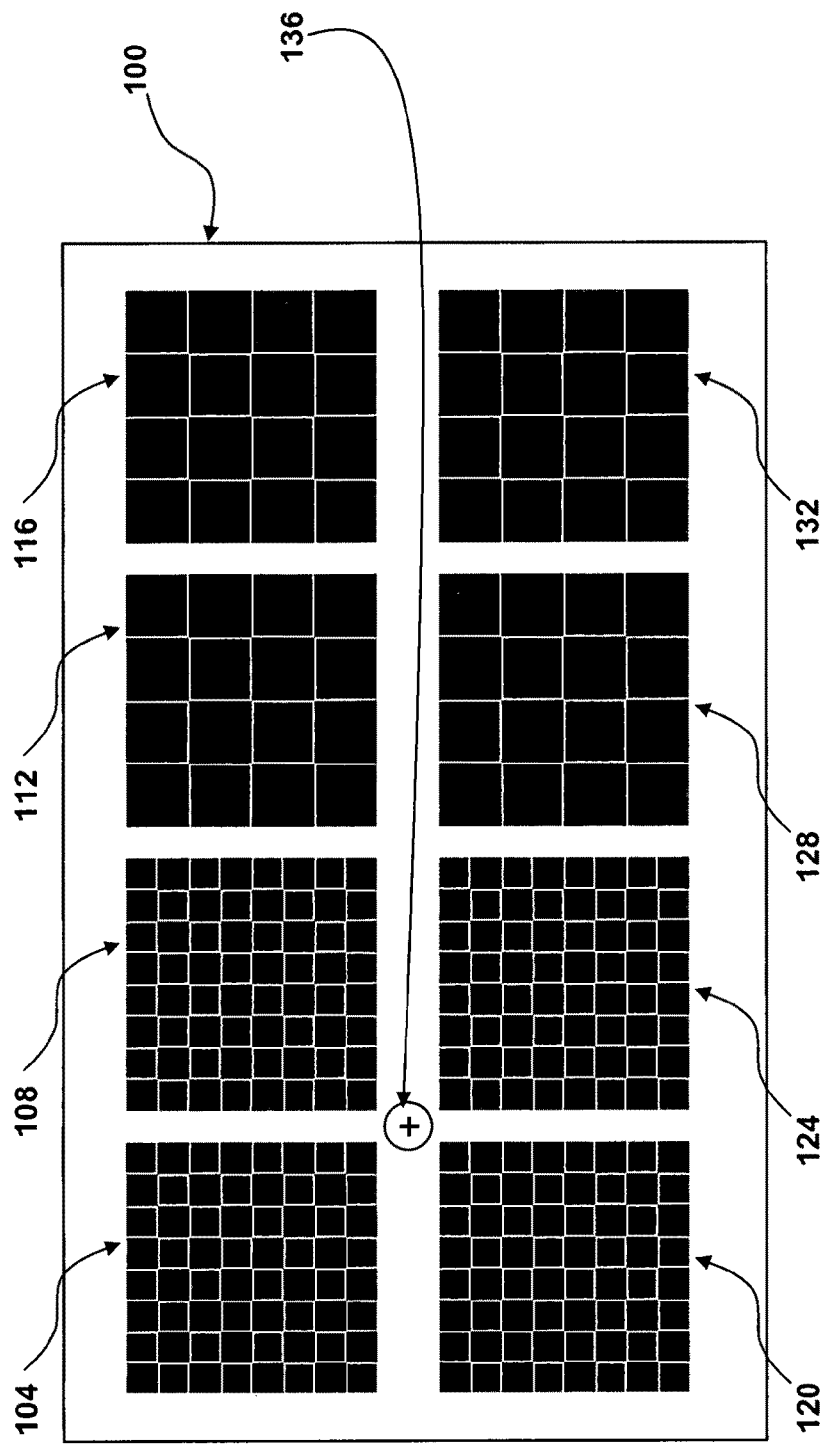
FIG. 1 illustrates a display to be shown to the right eye of a subject as part of a simultaneously multi-temporal visual test for determining a likelihood of a visual deficit in a subject, comprising visual patterns according to the present disclosure.

The present disclosure is drawn to methods and apparatuses for determining the likelihood of a visual deficit in a subject. The term "visual deficit" refers not only to deficiencies, defects, injuries, or impairments in one or both of a subject's eyes, but also to deficiencies, defects, injuries, or impairments along the entire visual pathway. The present disclosure can determine the likelihood of a deficits not only in the structural elements of an eye (iris, cornea, anterior chamber, posterior chamber, vitreous humor, lens, fovea, macula, etc.), but also in the optic nerve, optic chiasm, optic tract, LGN, geniculostriate pathway, and visual cortex, in communication with one or both eyes. The likelihood of a number of known illnesses, disorders, and diseases may be determined using the disclosed methods, including (but not limited to) glaucoma; macular degeneration; macular dystrophy; retinitis pigmentosa; Laurence-Moon-Bardet-Biedl syndrome; Stargardt's disease; inflammation of the retina; inflammation of the choroid; Serpiginous Choroiditis; cortical blindness; cataracts; basic refractive problems; strabismus; and combinations thereof.

The present methods and apparatuses are for determining the "likelihood" of a visual deficit in a subject. This terminology is used to clarify that, while these methods and apparatus may in some cases be capable of diagnosing the presence of a specific visual deficit, they are more often capable of, or configured to, merely screen for the likelihood of a visual deficit of one or more kinds. This "likelihood" may be in the form of a binary determination ("yes" or "no") or may optionally report a numerical measure of probability ("10% likely"), although other determinations may also be made.

Thus the present methods and apparatuses are available to test a subject, and to refer the subject for further analysis if the likelihood of a deficit is found. Moreover, the device can render a numerical or graphical measurement of the likelihood of the presence of a deficit, and an operator or doctor can use this measurement to determine further action. Further, the disclosed methods and apparatuses may indicate a deficit corresponding to multiple specific illnesses, without being able to further differentiate, and may require additional testing to isolate the specific disorder producing the identified deficiencies. Finally, although not described herein, the present apparatuses and methods may be combined with one or more screening devices (such as devices for physically scanning the eye) to advantageously increase the device's sensitivity, or to allow for a more definite identification of the presence of a specific disease or disorder, through the use of two or more assessment techniques.

The present disclosure teaches a simultaneously multi-temporal visual test. The term "simultaneously multi-temporal" means that patterns are visually presented to two or more different regions of the visual field of a subject's eye at the same time, and that these patterns vary over time at different rates, or at different phases, or at different rates and phases. A non-limiting example of such a variation which may occur over time is checkerboard contrast reversal, although other variations may be used, such as grating contrast reversals, isoluminant chromatic contrast functions, alternating sine-wave stripe patterns, isoluminant red-green stripe patterns, blue gratings with yellow backgrounds, or any other color reversal.

One advantage of a simultaneously multi-temporal visual test is that the testing process may be performed expediently, as multiple regions of the visual field are tested simultaneously. A further advantage is that tests may be performed with a minimum of instruction, where the subject is merely asked to focus on one area of the screen, while large areas of his visual field are tested. This simplicity allows tests to be performed on the young, the old, the infirm, those who have language impairments, and those whose language differs from that of the doctor or tester.

A still further advantage of a simultaneously multi-temporal visual test is that the simultaneous activation of multiple visual field regions discourages subjects from looking directly or inadvertently at a varying display pattern. In some single-temporal tests, in which regions of the visual field are individually activated, subjects can purposefully or inadvertently focus their vision on the single activated region, thereby testing only the foveal region of the eye. This is less likely to occur when multiple regions are activated, and even prelingual subjects are naturally discouraged from foveation on a single pattern in the display when two or more patterns vary simultaneously.

Although the simultaneously multi-temporal variations are experienced simultaneously by the subject, the responses of the subject's visual system to each pattern's distinct variation may be resolved by way of a frequency deconvolution or separation, such as (as a non-limiting example) a Fourier transform. Visual evoked potentials (VEPs) captured over the visual cortex may be subjected to a Fourier transform, and separated into frequency components corresponding to the frequencies at which the patterns are varied. This is only one kind of frequency deconvolution, however, and other may be used, including (as non-limiting examples) statistical minimization of mutual information rates, integral transforms, general spectral factorization over orthonormal bases, and wavelet transforms.

One advantage of the use of VEPs is that the subject does not need to give an overt or verbal response to a stimulus, as the VEP is naturally and unconsciously produced during vision. This not only allows testing of (as above) the young, the old, the infirm, those who have language impairments, and those whose language differs from that of the doctor or tester, but also avoids false information from the subject, who for any number of reasons may wish to conceal a visual impairment. A further advantage is that the VEP represents the visual response as initiated in the eye and carried to the visual cortex. Accordingly, and as noted above, the VEP captures impairments at any point or structure along this pathway, thereby determining the likelihood of more possible impairments than a mere eye exam can.

As a non-limiting example, two patterns may be shown to a subject simultaneously. The patterns may reverse in contrast at a rate of 15 Hz and 18.75 Hz, respectively. Then, VEPs captured over the visual cortex of the subject may be resolved into at least a 15 Hz component and an 18.75 Hz component. These "frequency components" may each have a phase and a magnitude.

The phase of each frequency component may be compared to the phase at which the patterns reverse, and the calculated phase offset can be used in determining the likelihood of a visual deficit. As a non-limiting example, the phase offset is expected to be correlated with the length of the pathway traveled from the eye to the visual cortex, and large phase offsets may indicate pathway impairments. Phase offsets of zero may also indicate acquisition errors, where the acquisition equipment (such as an electrode or sampling device) has inadvertently picked up the oscillating signal driving the pattern's contrast reversal.

Alternatively or additionally, the magnitude of each frequency component can be used in determining the likelihood of deficiencies. Frequency components with low magnitudes may indicate, as a non-limiting example, that the subject sees very little of the associated pattern reversing at that frequency, due to impairment in the physical structure of the eye or visual pathway, in regions corresponding to or in communication with the area of the visual field to which a pattern was shown varying at that frequency. Magnitudes obtained from frequencies corresponding to two different regions of the eye or eyes may be compared to each other, or to the mean magnitude of all frequency components, to determine if the magnitude is significantly low. Alternatively, magnitudes may be compared to a fixed expected response magnitude.

Alternatively or additionally, a summed magnitude of a subset of the frequency components may be compared to a summed magnitude of a second subset of the frequency components. As a non-limiting example, the first subset may include frequency components corresponding to display frequencies displayed in the superior half of the subject's visual field, and the second subset may include frequency components corresponding to display frequencies displayed in the inferior half of the subject's visual field. As another non-limiting example, the first subset may include frequency components corresponding to display frequencies displayed in a nasal portion of the subject's visual field, and the second subset may include frequency components corresponding to display frequencies displayed in a temporal portion of the subject's visual field. By summing the responses, signal-to-noise ratios may be improved and measurement errors may be reduced. Also, diagnoses of deficits across a broad region of the visual field may be obtained when data acquired for a narrow region is insufficient, inconclusive, or unnecessary.

Alternatively or additionally, the magnitude of one of the frequency components resolved from the testing of one eye may be compared to the magnitude of a corresponding one of the frequency components resolved from the testing of the other eye in a mirror-isometric region.

Additionally, confidence intervals may be determined for each frequency component measurement. As a non-limiting example, these confidence intervals may be obtained by way of $T^2_{circ}$ statistics for inter-test variability, although many other statistics are known for confidence measurements and may be used, including as a non-limiting example Least Square Error statistics which maximize the $R^2$ coefficient for inter-suite variability. These confidence intervals may be obtained immediately during testing, thereby allowing a testing operator to repeat a given test if the confidence intervals are too large. Alternatively, these confidence intervals may be obtained during later, post-test, analysis.

Although the test described above has two patterns at two frequencies, in two regions of the visual field, it should be noted that any number of regions may be activated at once, with different frequencies, phases, or both. It is often advantageous to use inharmonic frequencies, to assist in the deconvolution of the frequency components. The use of inharmonic frequencies avoids crosstalk, which is not only detrimental to deconvolution but moreover can appear like alpha or beta waves, making removal of alpha and beta waves from the data difficult. However, harmonic frequencies may sometimes be used, especially if the display refresh rate limits the number of available frequencies which may be shown. Alternatively or additionally, the patterns may be displayed at different phases, to aid in the deconvolution and to test for false readings.

Making reference to FIG. 1, a display 100 is shown comprising visual patterns 104, 108, 112, 116, 120, 124, 128, 132. The display 100 is expected to be viewed by the right eye of a subject, who would direct his gaze toward (or foveate on) focus point 136. Accordingly, patterns 104 and 120 would appear in the left, "nasal" portion of the visual field of his right eye, while patterns 108, 112, 116, 124, 128, and 132 would appear in the right, "temporal" portion of the visual field of his right eye. Similarly, patterns 104, 108, 112, and 116 would appear in the upper, "superior" portion of the visual field of his right eye, while patterns 120, 124, 128, and 132 would appear in the lower, "inferior" portion of the visual field. In a simultaneously multi-temporal visual test, patterns are shown to two or more different regions; as a non-limiting example, patterns 104 and 120 may be shown to the right nasal superior and right nasal inferior regions, respectively. These patterns vary in time, as will be explained with reference to FIG. 4 below.

Figure 2:
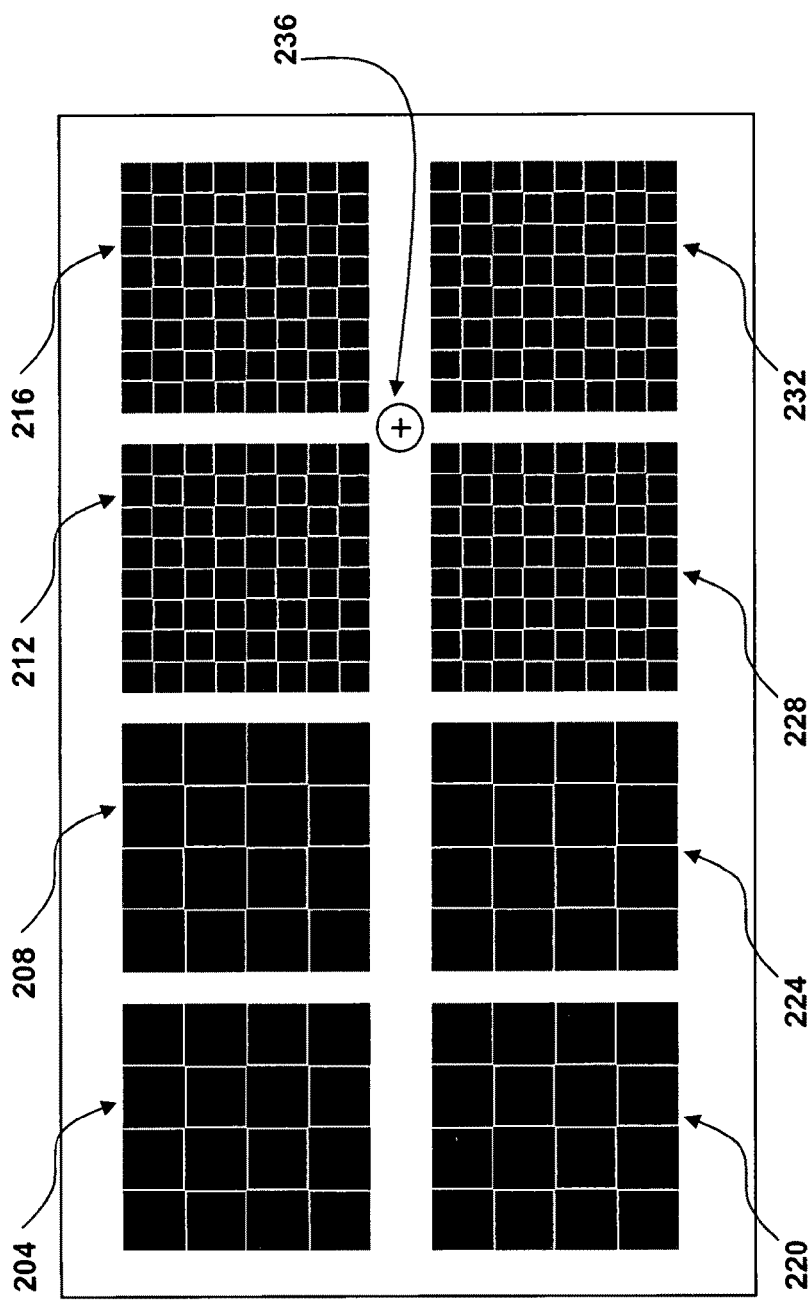
FIG. 2 illustrates a display to be shown to the left eye of a subject, comprising visual patterns according to the present disclosure.

Making reference to FIG. 2, a display 200 is shown. Unlike FIG. 1, this display 200 is expected to be viewed by the left eye of a subject. Accordingly, focus point 236, to which the subject would be expected to direct his gaze, is shown at the right side of the display. Again, two, patterns 216, 232 would appear in the right, "nasal" portion of the visual field of his left eye, while six patterns 204, 208, 212, 220, 224, and 228 would appear in the left, "temporal" portion of the visual field of his left eye. As in FIG. 1, four patterns 204, 208, 212, 216 would again appear in the upper, "superior" portion of the visual field of his left eye, while the other four patterns 220, 224, 228, 232 would appear in the lower, "inferior" portion of the visual field. In some aspects of the present method, a test is performed at least once for the subject's right eye and at least once for the subject's left eye. As shown, the patterns for the right eye and the patterns for the left eye may be shown to mirror-isometric regions of the first and second visual fields.

Although eight patterns are shown in the displays of FIGS. 1 and 2, and may be shown to the subject at the same time as illustrated (four patterns in a superior region and four patterns in an inferior region), any number of patterns may be used, depending on the time constraints of the test and the resolving power of the acquisition and sampling equipment. That is, although eight patterns may be simultaneously shown to a subject, and varied in time at different rates, resolving eight distinct frequency components from a VEP can lead to a low signal-to-noise ratio, and render the result inconclusive. In addition, it may be difficult for a subject to remain focused on one area of a display when eight contrast-reversing patterns are flickering across the visual field. Accordingly, in one aspect of the disclosed method, described in the following paragraphs, two patterns are shown at a time, progressing from nasal to temporal locations at a fixed rate.

Figure 3B:
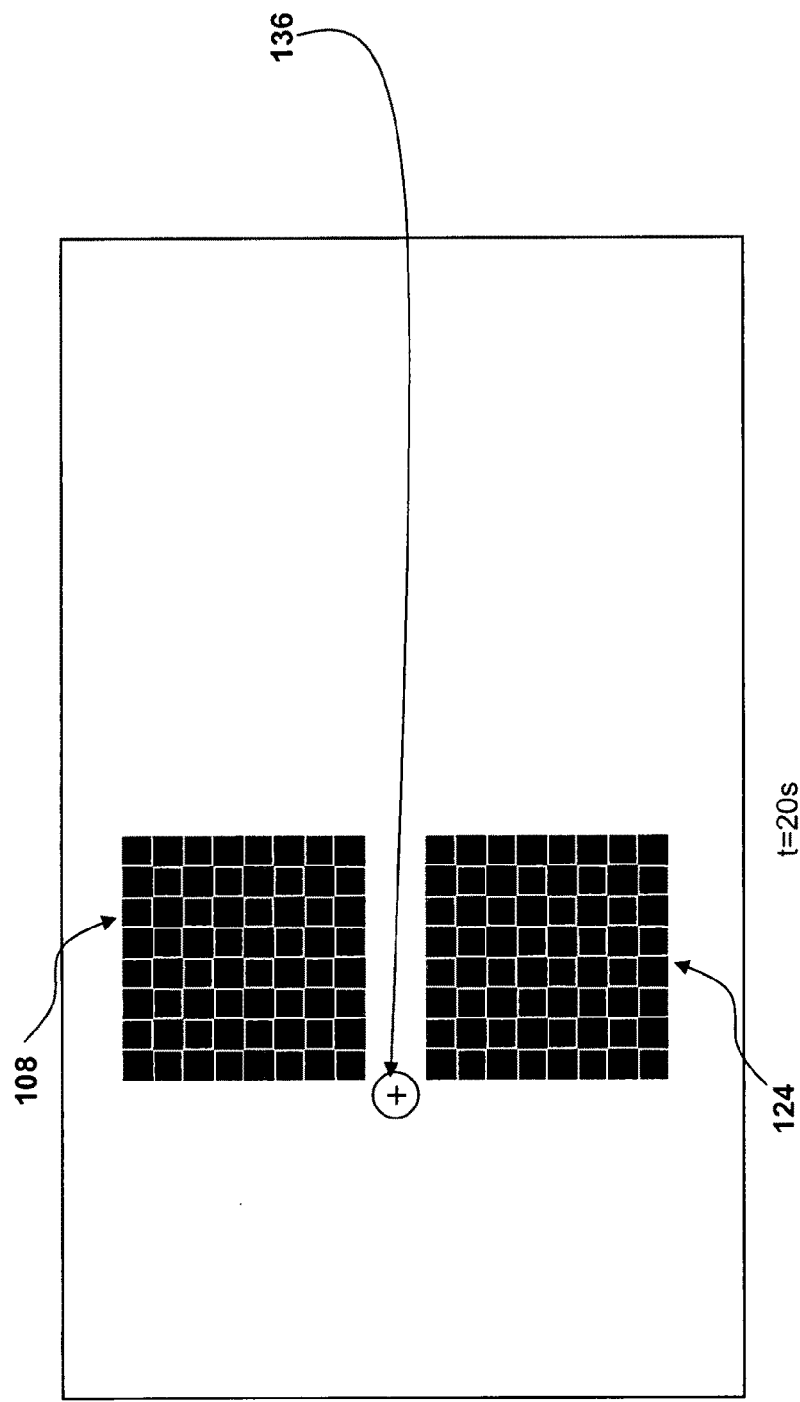
Figure 3C:
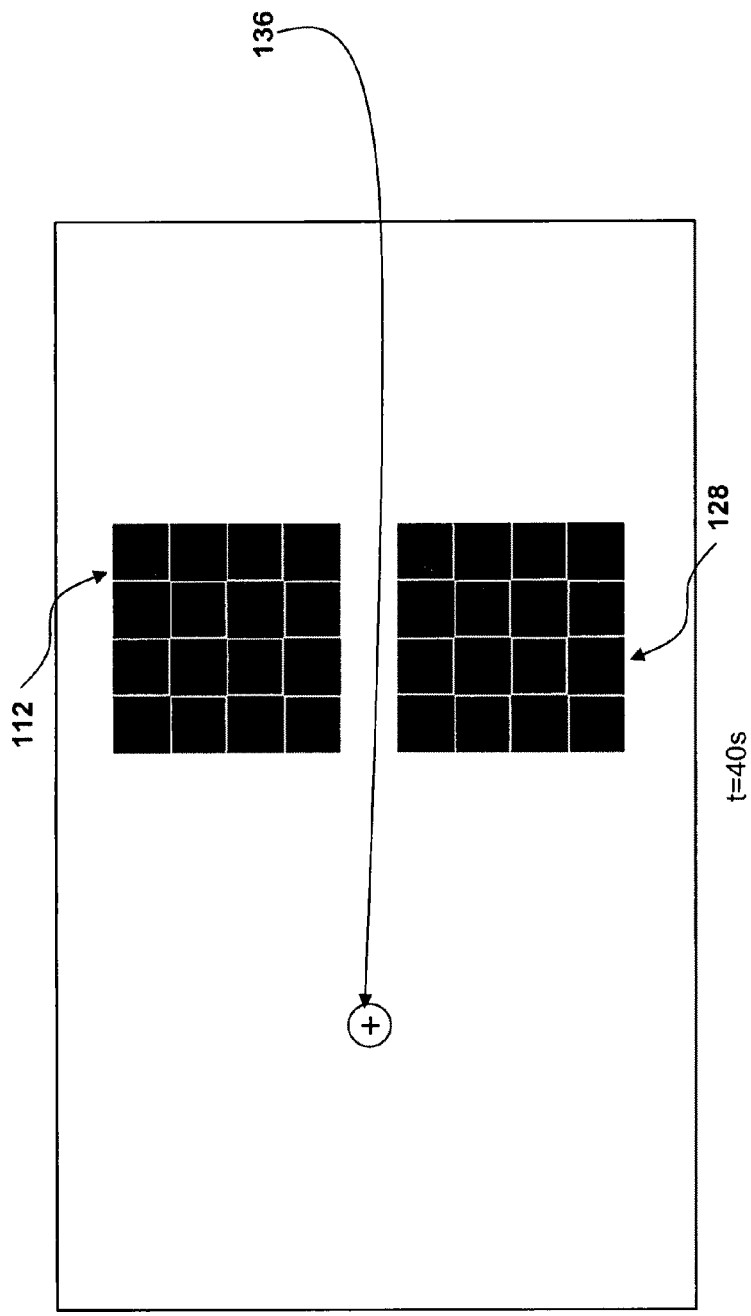
Figure 3D:
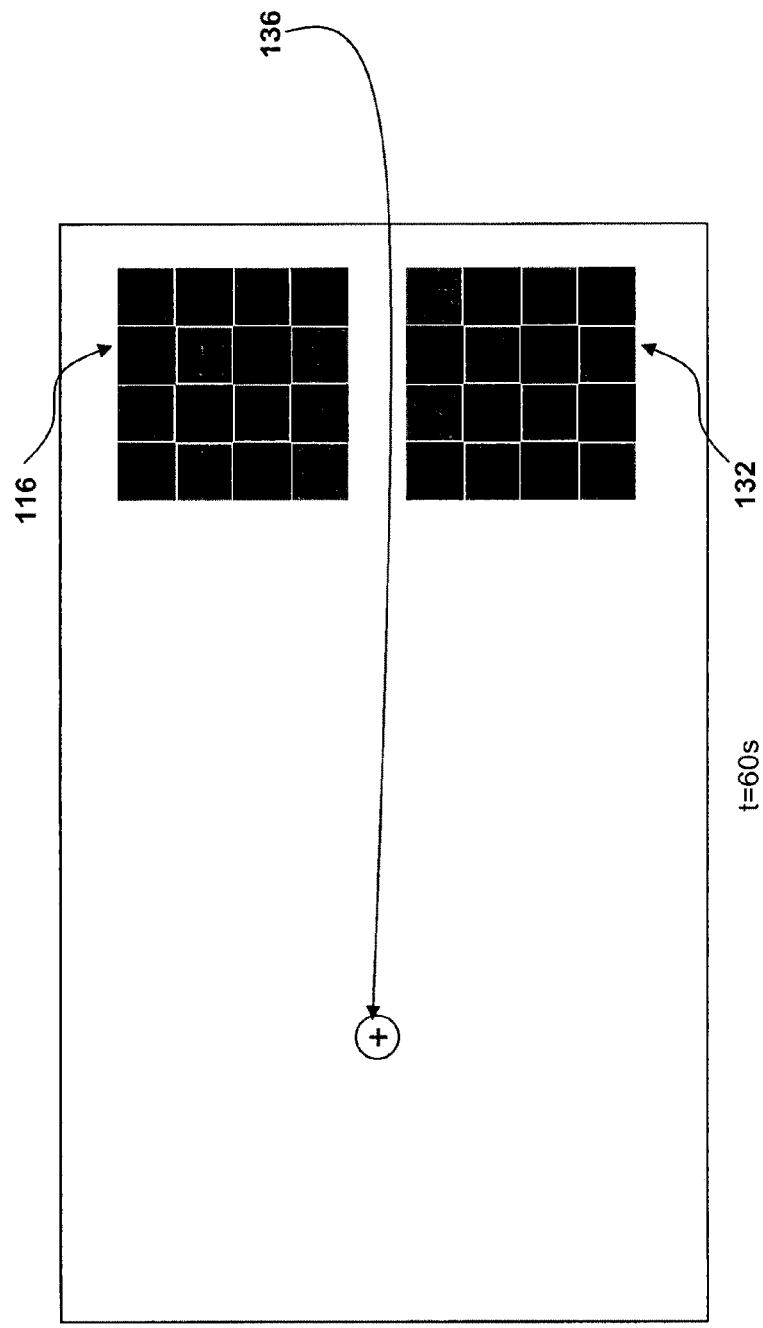

FIGS. 3a-3d show a non-limiting example of a sequence progressing in this manner. In FIG. 3a, two patterns 104, 120 are shown to the subject's right eye in superior and inferior nasal locations. (The subject's left eye may be covered, so that only the right eye is being stimulated by the contrast reversals). As above, the subject fixates on focus point 136, while patterns 104 and 120 undergo contrast reversals at different frequencies. During this period, electrical activity is captured from the brain of the subject by use of electrodes, as will be described in greater detail below. The sequence begins at time t=0 (element 300). In this non-limiting example, a testing period of twenty seconds is used; this is only one example, however, and tests in one area may be performed in as little as five seconds, or as many as 60 seconds, so long as the acquisition hardware and software can resolve a sufficiently clean and statistically significant response. Signals corresponding to the acquired electrical brain activity may be immediately analyzed, or preferably may be digitized and stored for later analysis.

When the first twenty seconds of testing have elapsed, patterns 104 and 120 are no longer shown, and as in FIG. 3b, patterns 108 and 124 are shown in a more temporal location. Fixation is maintained on focus point 136, and another twenty seconds of contrast reversal occur, beginning at time t=20. Similarly, once forty total seconds of testing have elapsed, patterns 108 and 124 are no longer shown, and, as in FIG. 3c, patterns 112 and 128 are shown in an even more temporal location. Again, fixation is maintained on focus point 136, and another twenty seconds of contrast reversal occur. Once sixty total seconds of testing have elapsed, patterns 112 and 128 are no longer shown, and, as in FIG. 3d, patterns 116 and 132 are shown in the furthest temporal location. Once again, fixation is maintained on focus point 136, and another twenty seconds of contrast reversal occur. The signal corresponding to the acquired electrical brain activity may be stored in a manner that indicates the visual field regions stimulated at the time of recording, and thus the regions to which the data corresponds.

Figure 4A:
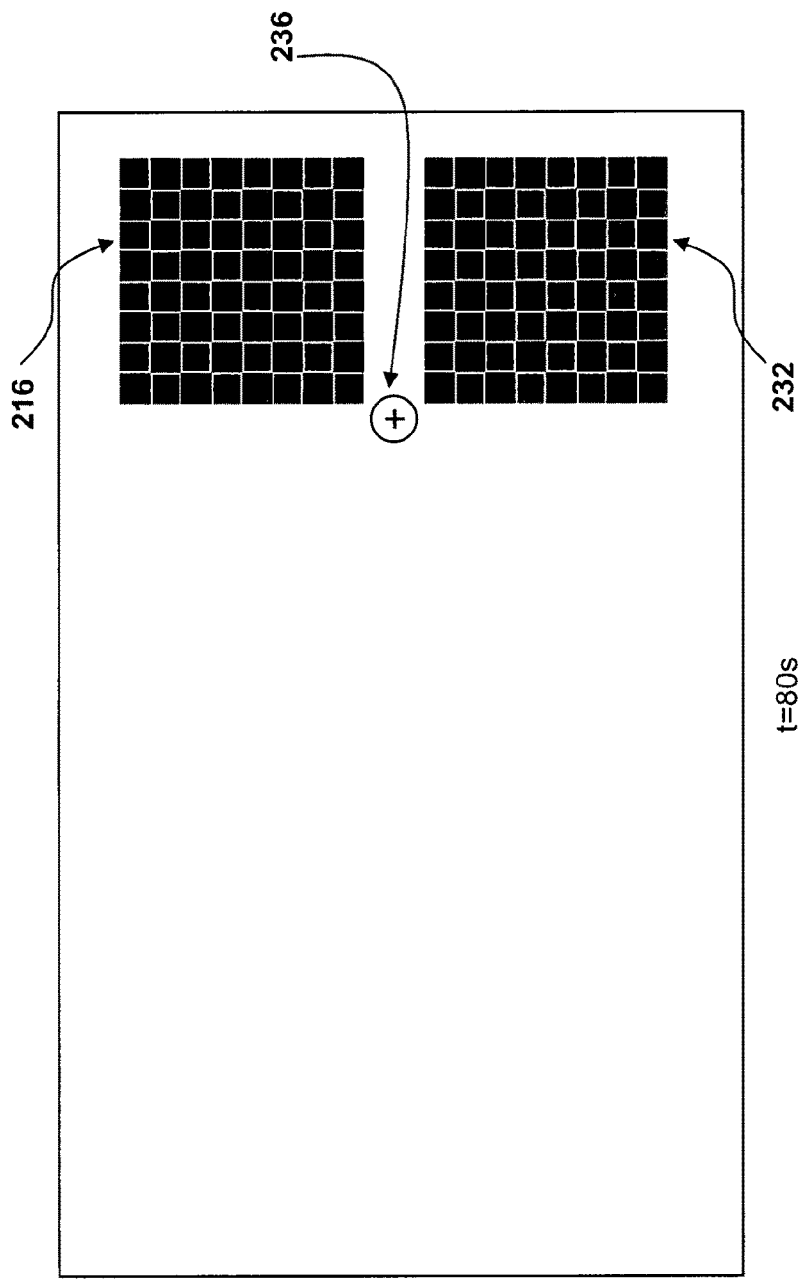
Figure 4B:
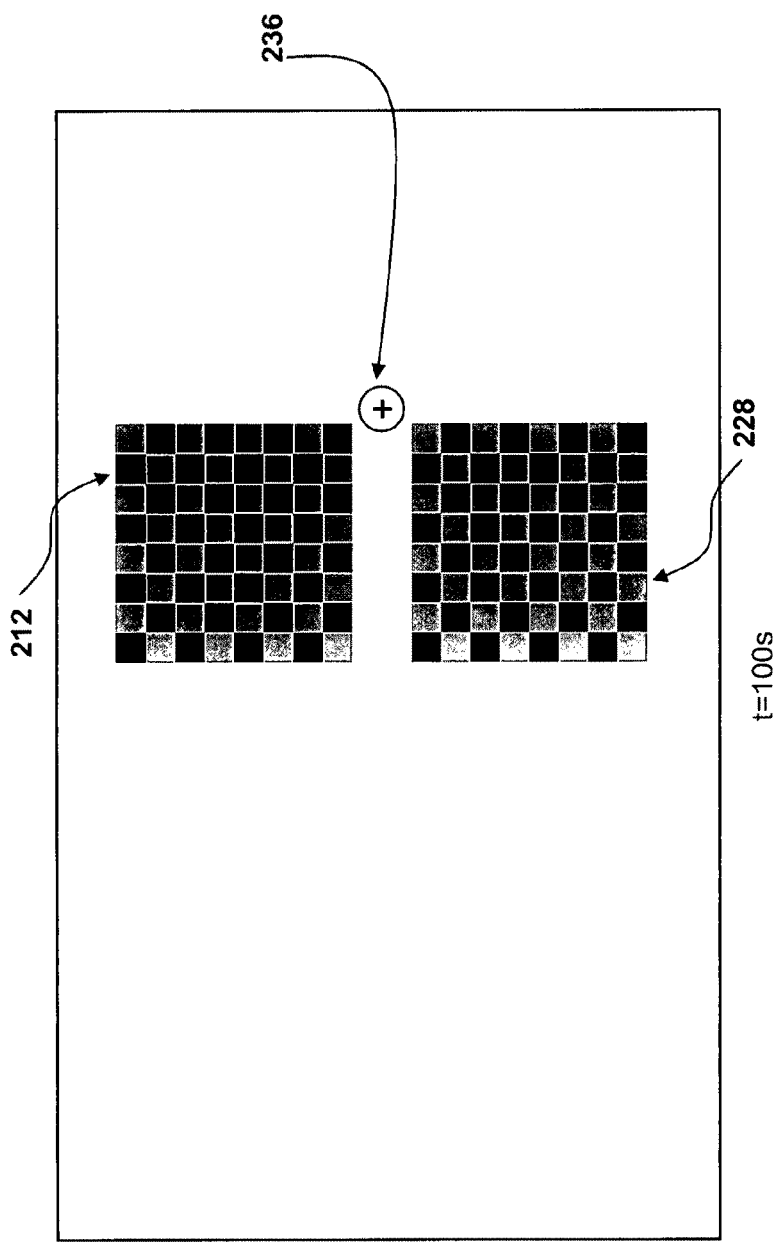
Figure 4D:
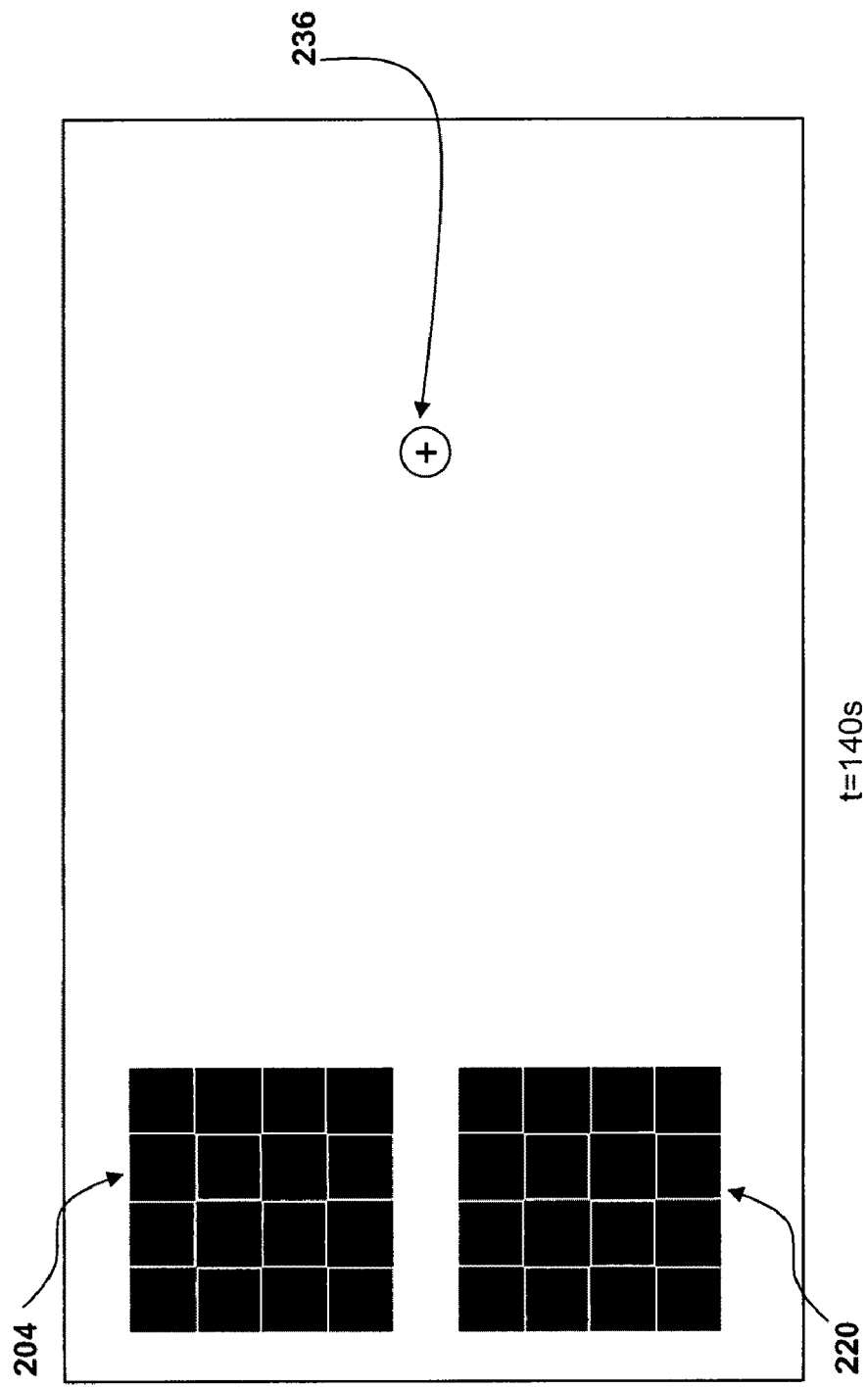

At this point, testing of the right eye is complete. If the left eye is to be tested, then the right eye may now be covered, and the left eye uncovered, and left-eye stimuli as shown in FIGS. 4a-4d may be used. In FIG. 4a, two patterns 216, 232 are shown to the subject's left eye in superior and inferior nasal locations. As above, the subject fixates on focus point 236, while patterns 216 and 232 undergo contrast reversals at different frequencies. The sequence begins at time t=80s. When the next twenty seconds of testing have elapsed, patterns 216 and 232 are no longer shown, and as in FIG. 4b, patterns 212 and 228 are shown in a more temporal location. Fixation is maintained on focus point 236, and another twenty seconds of contrast reversal occur, beginning at time t=100 s. Then, patterns 212 and 228 are no longer shown, and, as in FIG. 4c, patterns 208 and 224 are shown in an even more temporal location. Again, fixation is maintained on focus point 236, and another twenty seconds of contrast reversal occur. Finally, as in FIG. 4d, patterns 208 and 224 are no longer shown, while patterns 204 and 220 are shown in the furthest temporal location. Once again, fixation is maintained on focus point 236, and a final twenty seconds of contrast reversal occur.

During the 160 seconds of testing described above, electrical activity of the brain of the subject may be acquired by electrodes, converted into a digital signal by a digital to analog converter, and optionally saved. During testing, or afterwards, one or more frequency components may be resolved from a signal corresponding to the electrical brain activity and analyzed for visual deficits, as described above.

Figure 5A:
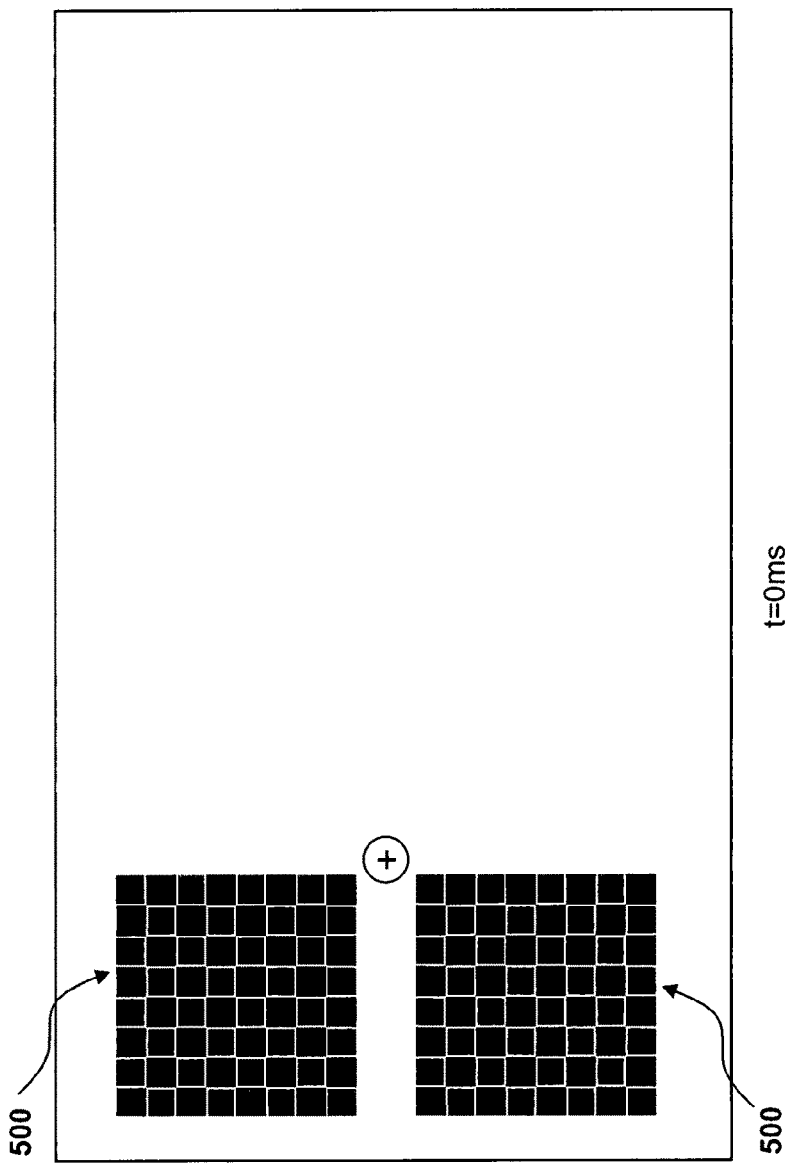

The above sequence demonstrates the progressive activation of different visual regions, but does not demonstrate in detail the way in which the contrast reversals themselves occur. To better illustrate these reversals, FIGS. 5a-5j illustrate in detail a portion of one sequence of contrast reversals for one region of the subject's visual field, over a period of two seconds. These two seconds could correspond to the first two seconds of any twenty second sequence described above. Here, two patterns are presented to the superior and inferior nasal regions of the subject's right eye's visual field. The patterns shown are checkerboard patterns of alternative light and dark squares evenly distributed across a larger square area. "Reversal" is said to occur when light squares are exchanged with dark squares, and dark squares are exchanged with light squares. Accordingly, the checkerboards alternate between two "configurations," 500 and 504. As a non-limiting example, the superior pattern is illustrated as reversing in contrast at a rate of 15 Hz, or 60 times every 4 seconds, while the inferior pattern is illustrated as reversing in contrast at a rate of 18.75 Hz, or 75 times every 4 seconds. Both patterns reverse in contrast with a phase of zero. Thus, at the beginning of the sequence, as shown in FIG. 5a, both patterns are in configuration 500.

Figure 5C:
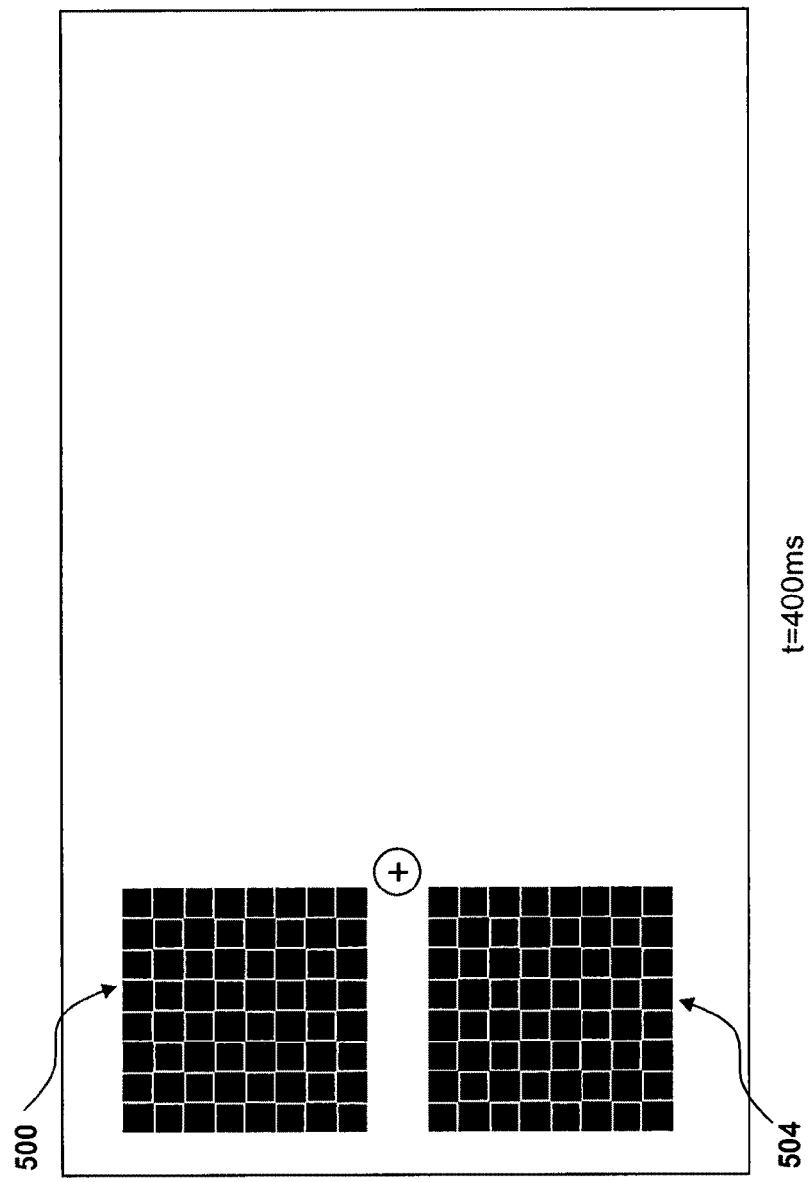

FIG. 5b shows the display at 200 ms after the sequence initiates. Here, the superior pattern has reversed three times, and is now in configuration 504, while the inferior pattern has also reversed three times and is in configuration 504. FIG. 5c shows the display at 400 ms after the sequence initiates. Here, the superior pattern has reversed three more times, and thus has returned to configuration 500, while the inferior pattern has reversed four times, and is again in configuration 504.

Figure 5F:
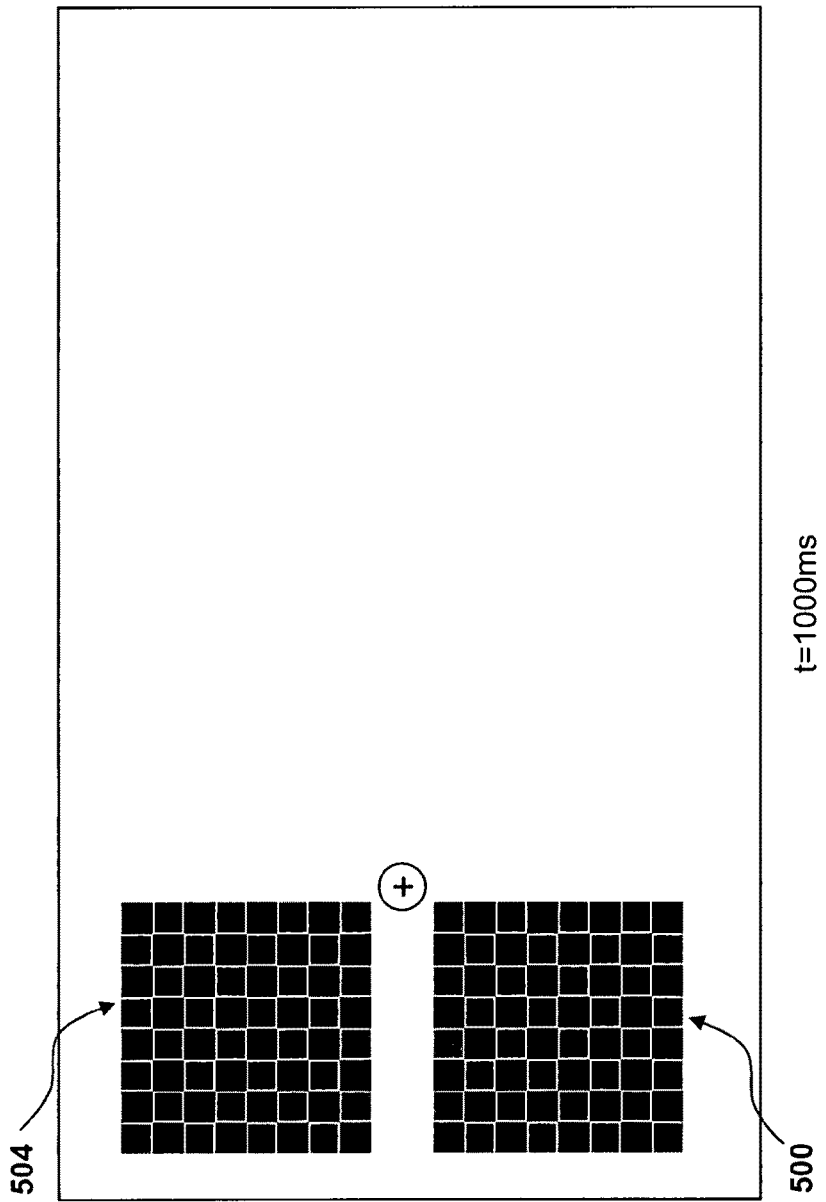
Figure 5H:
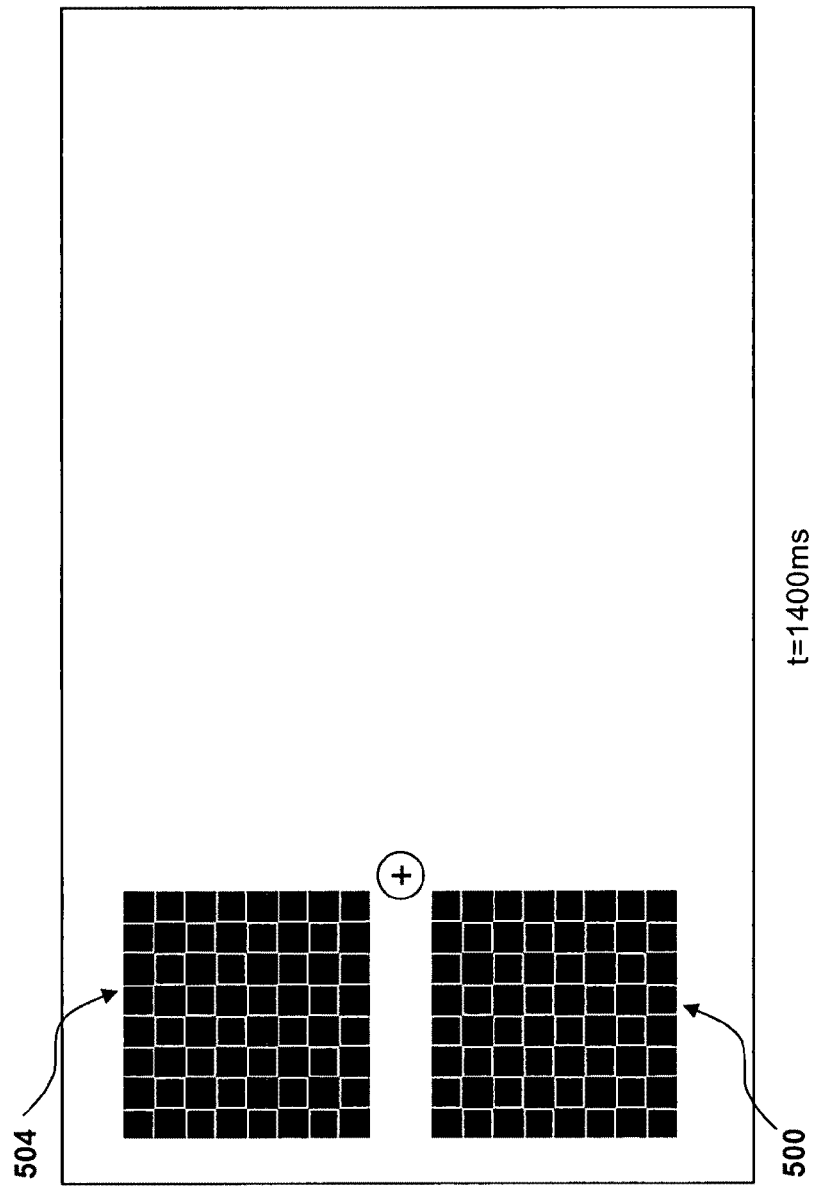
Figure 5J:
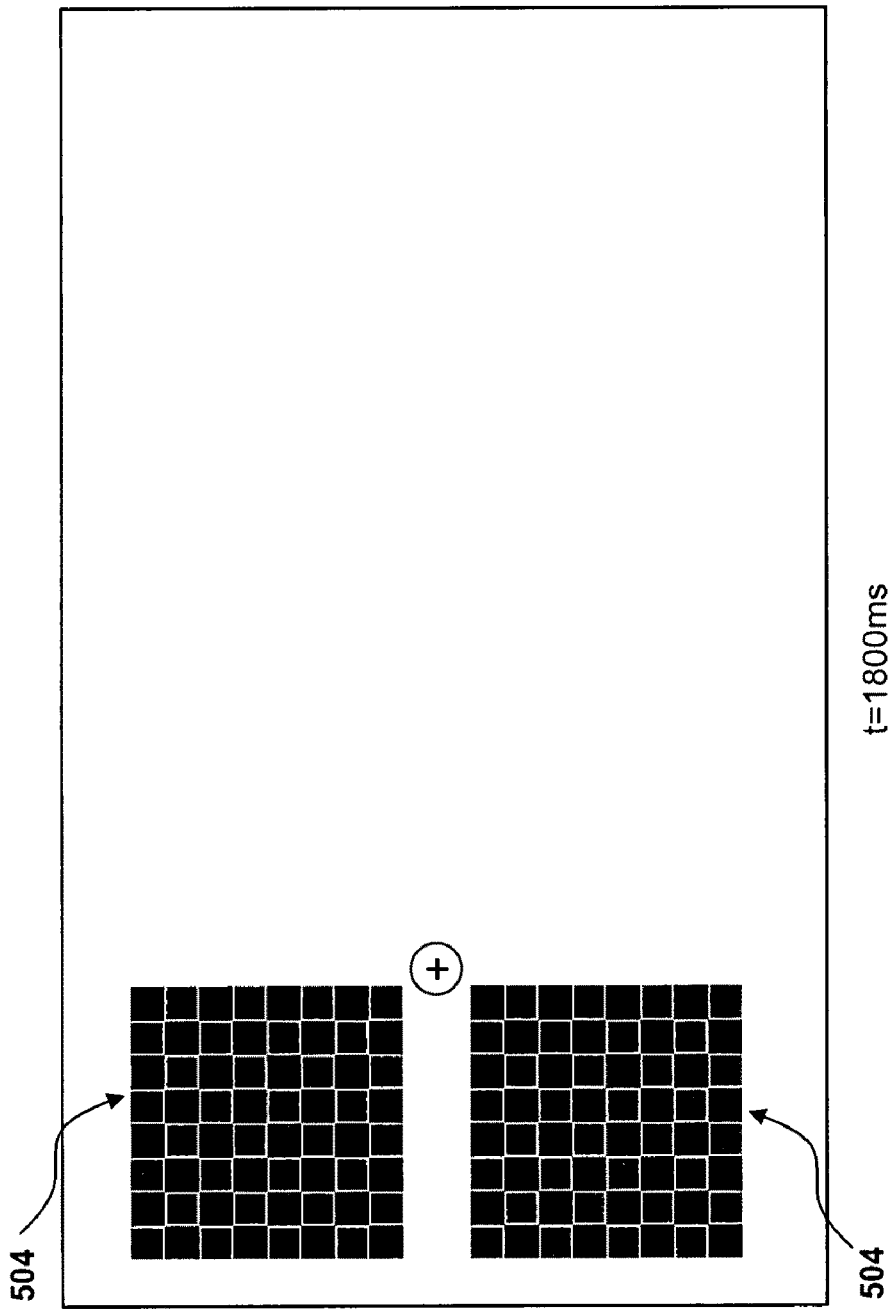

FIG. 5d shows the display at 600 ms after the sequence initiates. Here, the superior pattern has again reversed three times, and is in configuration 504, while the inferior pattern has reversed four times, and is this in configuration 504. FIG. 5e shows the display at 800 ms after the sequence initiates. Here, the superior pattern has reversed three times, and is in configuration 500, while the inferior pattern has reversed four times, and is in configuration 504. FIG. 5f shows the display at 1000 ms after the sequence initiates. Here, the superior pattern has reversed three times and is in configuration 504, while the inferior pattern has reversed three times, and is in configuration 500. FIGS. 5g, 5h, 5i and 5j show the display at 1200 ms, 1400 ms, 1600 ms, and 1800 ms after the sequence initiates, respectively. Contrast reversal continues in this manner for the duration of a test period, and then a new sequence begins in two more temporal locations. The same frequencies may be used in the new locations, or two different frequencies may be chosen.

From this illustration, it is clear that the two patterns alternate at different frequencies, which together lead to a composite VEP having at least two frequency components corresponding to the two distinct rates of contrast reversal. As described above, resolution of these components allows for separate determination of the likelihood of deficits in the superior and inferior nasal regions of the subject's right eye's visual field. While either of these regions could be independently tested, the simultaneously multi-temporal visual test provides the clear advantages described above, including a decrease in testing time, a decrease in undesirable gaze-shifting, and greater assurance that a target area of the visual field is in fact being stimulated.

Figure 6:
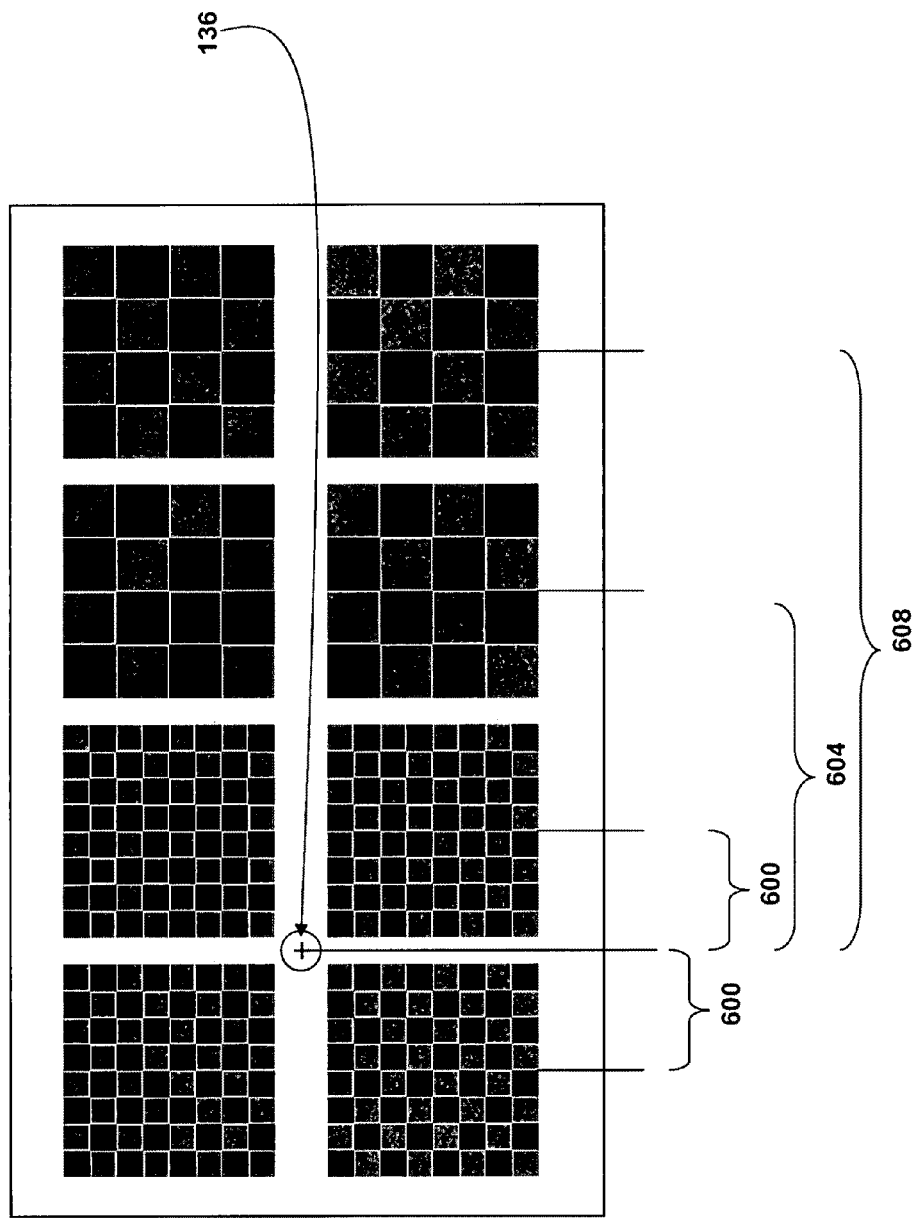
FIG. 6 illustrates spacing for a display to be shown to the right eye of a subject, comprising visual patterns according to the present disclosure.

The exact placement of the subject, display, and patterns may vary. FIG. 6 illustrates one exemplary configuration, in which the placement of the patterns on the display will now be described as a non-limiting example. As above, the subject fixates on focus point 136. The centers of the nearest patterns are horizontally displaced from this focus point by 36.6 mm (measurement 600). Proportionally, the next patterns are horizontally displaced from this focus point by 109.7 mm (measurement 604). The furthest patterns are horizontally displaced from the focus point by 182.8 mm (measurement 608). These measurements are chosen to control for the horizontal angle at which the patterns are observed at the subject's eye. At a viewing distance of 30 inches, which is typical for a general testing environment, the patterns displaced by 36.6 mm (measurement 600) are observed at a viewing angle of 2.74 degrees between the patterns and the focus point, those displaced by 109.7 mm (measurement 604) are observed at a viewing angle of 8.19 degrees, and those displaced by 182.8 mm (measurement 608) are observed at a viewing angle of 13.5 degrees. As the subject fixates on focus point 136, the observed viewing angle determines how far from the subject's fovea the image of the pattern is formed on the subject's retina. This is only one configuration, however, and many others are available. As a non-limiting example, a viewing distance of 15 inches may be used where, for example, testing space is at a premium, in which case the viewing angles will be doubled.

As Non-limiting Examples:
Visual patterns with low contrast may be displayed at over five degrees of displacement. Low contrast patterns are known to particularly activate the magnocellular pathway, including the cells less-densely populated cells in the eye. Accordingly, this combination of pattern and location may be used to test for glaucoma, which can lead to specific impairment in the magnocellular pathway.

Visual patterns with high contrast may be displayed at between 1.5 degrees and 5 degrees of displacement. High contrast patterns are known to particularly activate the parvocellular pathway, including the more-densely populated cells in the eye. Accordingly, this combination of pattern and location may be used to test for macular degeneration, which can lead to specific impairment in the parvocellular pathway.

As a quality control check on the above measurements, visual patterns with low contrast may be displayed between 1.5 degrees and 5 degrees from the subject's fovea, and visual patterns with high contrast may be displayed at over 5 degrees from the subject's fovea.

Checkerboard patterns of a first grid size may be displayed between 1.5 degrees and 5 degrees from the subject's fovea, and checkerboard patterns of a second grid size may be displayed over 5 degrees from subject's fovea, where the near checkerboard patterns reverse at a greater frequency than the far checkerboard patterns, and where the near checkerboard patterns are of a smaller granularity than the far checkerboard patterns, as illustrated in FIGS. 1 and 2. Variations in the size and distribution of checkerboard patterns allows for even more control over the contrast and luminance observed by the subject in a particular region of his visual field.

Figure 7:
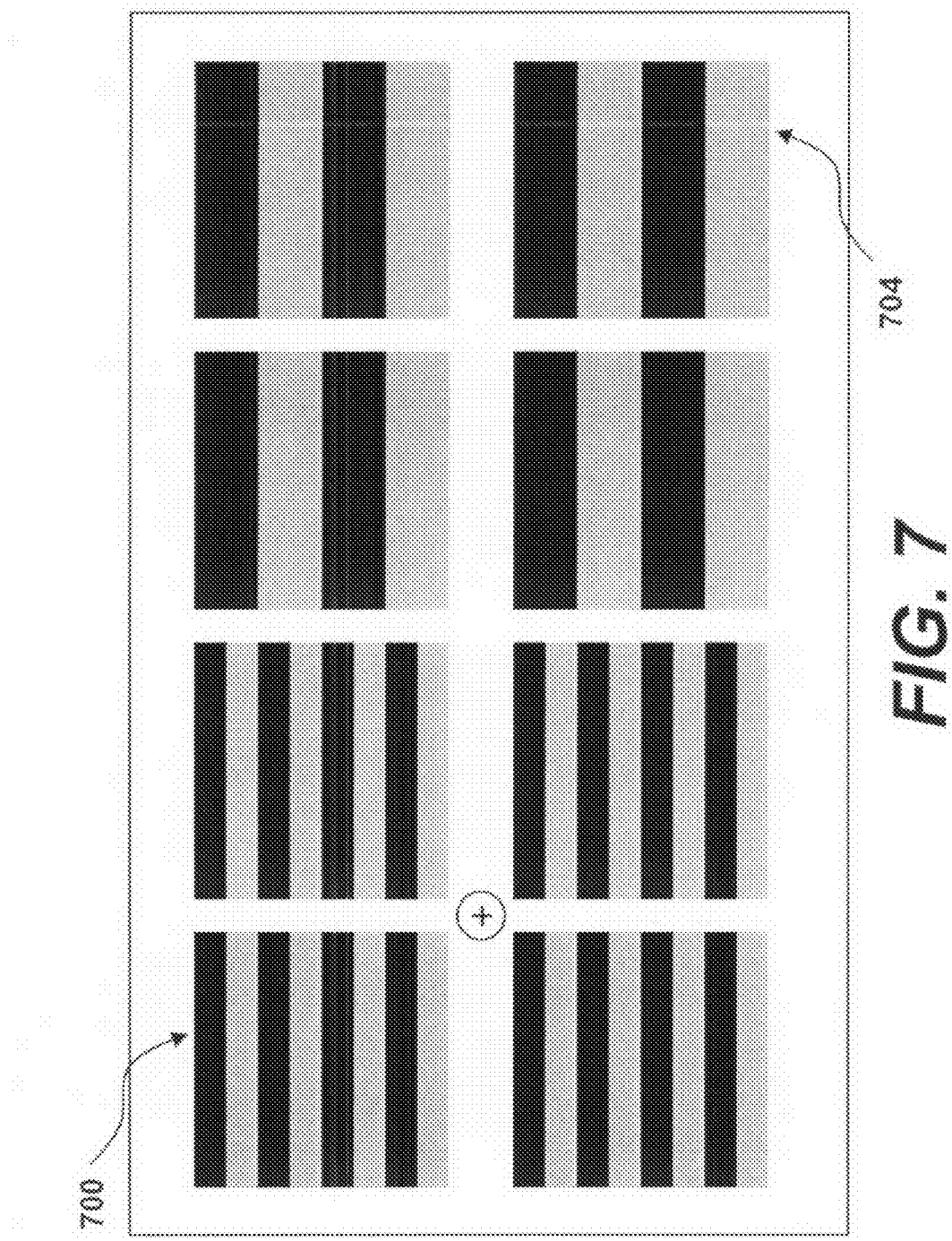
FIG. 7 illustrates another aspect of a display to be shown to the right eye of a subject, comprising visual patterns according to the present disclosure.

It should be noted that the checkerboards illustrated in the previous figures are merely one shape which can be used in contrast reversal, and that other shapes are known, including concentric circles, and, as shown in FIG. 7, thin stripes 700 and wide stripes 704.

Figure 8:
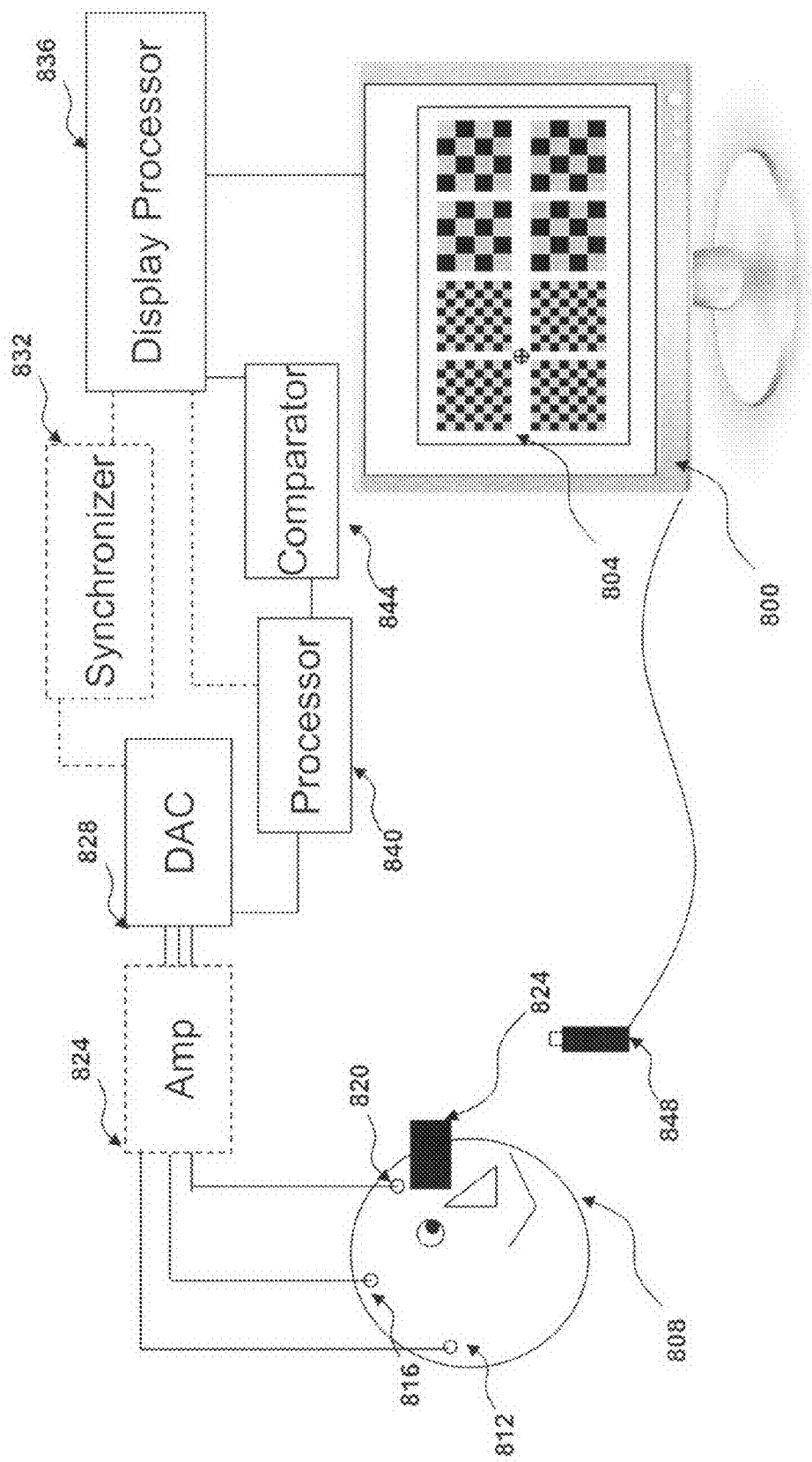
FIG. 8 illustrates an apparatus for determining a likelihood of a visual deficit in a subject by way of a simultaneously multi-temporal visual test according to the present disclosure.

FIG. 8 illustrates an apparatus for determining a likelihood of a visual deficit in a subject by way of a simultaneously multi-temporal visual test. A user 808 observes a visual display device 800 configured to simultaneously display at least two visual patterns 804 to one eye of the subject, in the manners described above. The other eye, that which is not being tested, may be covered by an opaque element 824 of any kind. Then, upon completion of one test, the opaque element 824 may be placed over the tested eye, and the untested eye may then be tested by way of further patterns. In this way, one eye can be tested at a time.

Electrodes 812, 816, and 820 are used to capture electrical activity of the brain of the subject during the test. In the non-limiting example embodiment of FIG. 8, electrode 812 is placed over the visual cortex of the subject (in the standard 10-20 system, at OZ), electrode 816 is placed at the midpoint between the subject's nasion and inion (CZ), and electrode 820 is placed at the front of the subject's head (FZ or FPZ, or nearby). Electrode 812 is used as a signal electrode, electrode 816 is used as a reference electrode (against which the signal from electrode 812 is calculated), and electrode 820 is used as a ground electrode. This is merely one non-limiting example of electrode placement, however, and the presently disclosed methods and apparatuses may functions with the use of multiple electrodes for capturing VEPs or other evoked potentials, or with different placements of reference and ground electrodes. Those skilled in evoked potential acquisition are aware of other systems for electrode placement, which provide different advantages in acquiring certain evoked potentials and not others, or which provide greater comfort to the user.

The electrodes are connected to an optional amplifier 824, which amplifies the electrical signals corresponding to the evoked potentials. A digital-to-analog converter 828 then digitizes the (optionally amplified) electrical signals, by sampling the electrical brain activity and producing a corresponding digital signal. The digitization may occur at a chosen sampling rate, or may be triggered by a synchronizer 832 so as to be synchronized with the display 800 whose patterns 804 are generated by a display processor 836. As a non-limiting example of such synchronization, synchronization may occur by way of interrupt signals, as described in U.S. Pat. No. 6,475,162 to Hu et al., the contents of which are incorporated herein by reference in their entirety.

A processor 840 may be configured to resolve one or more frequency components from the digital signal. These components may be resolved by way of a Fourier transform, although other methods of isolating frequency components may be used. One or more of the frequency components resolved may corresponding to a display frequency. Optionally, additional frequency components may be resolved, corresponding to electrical signals and noise known to interfere with measurement of VEPs. As a non-limiting example, frequencies corresponding to alpha or beta waves may be extracted, and their effect accounted for, or removed from the overall signal before any determining step occurs. As a further non-limiting example, frequencies corresponding to household electrical signals and noise (at 55 or 60 Hz) may be resolved and optionally removed. As a still-further non-limiting example, frequencies which correspond to large artifacts such as an eye blinks may be removed in this manner as well, or by use of a standard high-pass or band-pass filter.

Once frequency components corresponding to display frequencies have been resolved, a comparator (optionally a part of processor 840, or alternatively a separate element 844) may then determine a measurement of a likelihood that a visual deficit exists in a visual area corresponding to a visual field area to which a pattern was displayed. This can be accomplished in a number of manner, some of which are as follows.

The processor 840 may resolve the phase of each frequency component, and the comparator 844 may compare the phase of each frequency component to the phase of the corresponding visual pattern display to compute a phase match measurement for each frequency component.

The comparator 844 may compare the magnitude of one of the frequency components to the magnitude of another of the frequency components.

The comparator 844 may compare magnitudes of a first subset of the frequency components to magnitudes of a second subset of the frequency components to determine a likelihood that a visual deficit exists in a visual area corresponding to a visual field area to which a pattern was displayed. As noted above, these first and second subsets may correspond to the upper and lower halves of the subject's visual field.

A button or other behavioral response device 848 may be provided to the subject, with which he may perform a behavioral task to aid in securing attention and foveation, as described below with reference to FIGS. 10a-10d.

All of the above elements may in some aspects be housed at a single machine, which may advantageously be made mobile. In this way, a testing device may be carried to any location where testing is to be performed. The machine may have a keyboard, mouse, and display for an operator to use, and a separate display on which patterns are shown to a subject, and the device may provide feedback to the operator on the test, such as a measurement of the alpha wave size of the subject (indicating the subject's attention level), or whether sufficient or statistically significant VEPs have been obtained for display to a particular region of the visual field. Feedback may also be provided of any behavioral responses made by the subjects, or of the number and size of artifacts (such as eye blinks) which occur.

Making general reference to FIG. 8, the present disclosure also includes a system for determining a likelihood of a visual deficit in a subject by way of a simultaneously multi-temporal visual test. The system includes means for simultaneously displaying at least two visual patterns to the subject (such as display 800). Each pattern reverses in contrast or color at a different one of a corresponding number of display frequencies, and each pattern is displayed to a different region of the subject's visual field. The system also includes means for resolving one or more frequency components (such as processor 840), each corresponding to a different display frequency from electrical activity captured from the brain of the subject. The system also includes means for determining from one or more of the frequency components a measurement of a likelihood that a visual deficit exists in a visual area corresponding to the visual field area to which a pattern alternating at the one of display frequency was displayed (such as comparator 844 together with processor 840).

Figure 9:
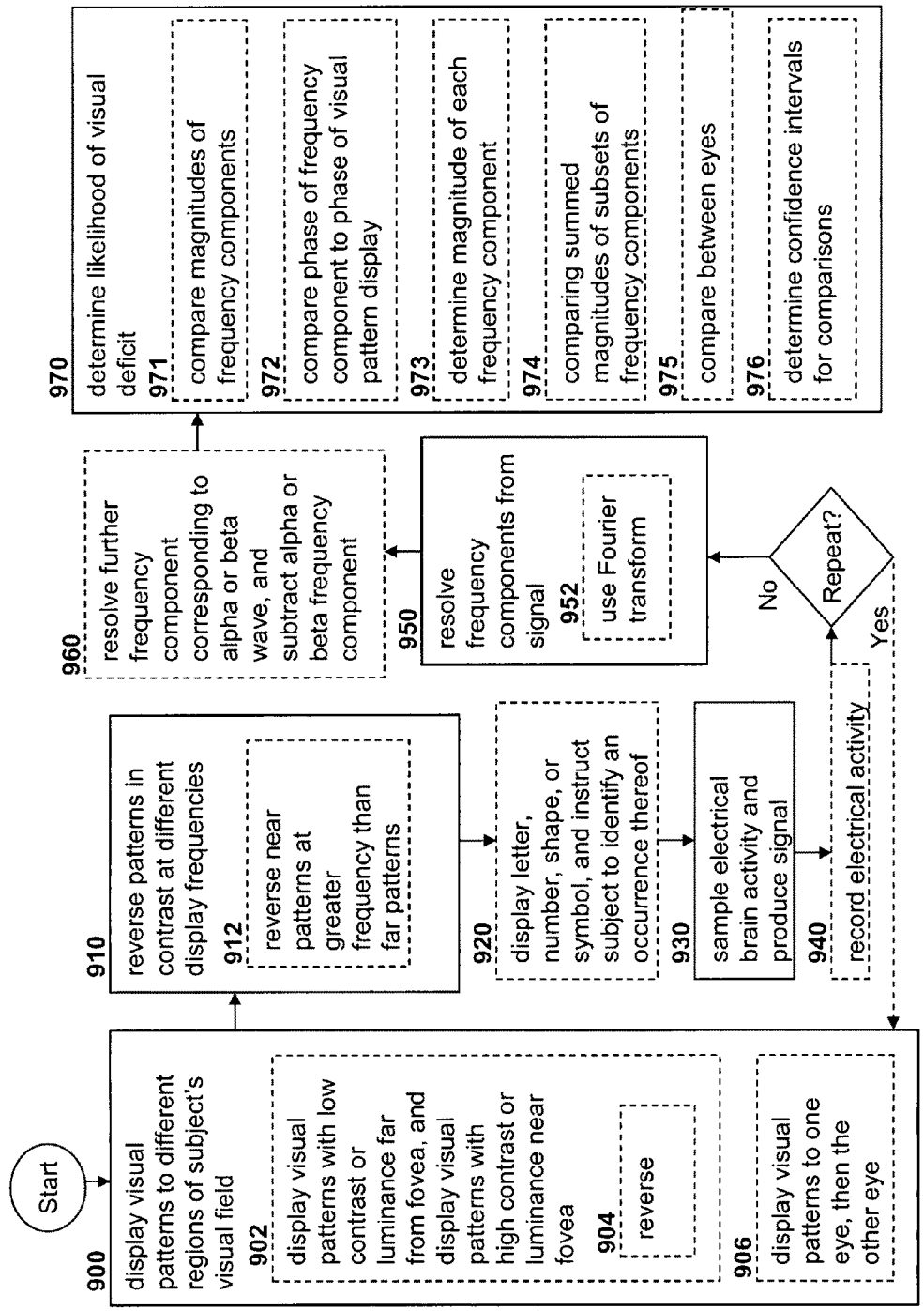
FIG. 9 charts a method for determining a likelihood of a visual deficit in a subject by way of a simultaneously multi-temporal visual test according to the present disclosure.

One non-limiting example of a method for determining likelihood of a visual deficit in a subject according to the present disclosure will now be described with reference to FIG. 9. While one order of steps is disclosed in the chart of FIG. 9, this order is a non-limiting example, and those skilled in the art will realize that other orders are possible. For example, the subtraction of alpha or beta waves (step 960) may be performed before or after the resolution of frequency components (step 950). In FIG. 9, optional steps are marked with a dashed line, and are not intended to limit the overall scope of any methods claimed herein. Steps shown inside of other boxes (for example, step 971 shown inside of step 970) recite optional specific methods or additional steps which may be used to enhance or complement the parent step. Again, the full scope of the method is defined by the claims below.

Making reference to FIG. 9, two or more visual patterns are shown to two or more regions of a subject's visual field (step 900). The subject is instructed to focus his eyes at an identified point, so that the visual patterns are known to be shown to specific regions of the eye not directly on the fovea. In some aspects, visual patterns with low contrast are shown far from the fovea, and visual patterns with high contrast are shown near to the fovea, simultaneously or separately, to isolate the magnocellular and parvocellular pathways (optional step 902). These pattern placements may then be reversed (optional step 904) to serve as a quality check. The test may be performed for one eye, and then for the other eye (optional step 906).

Wherever the visual patterns are shown, the patterns undergo contrast reversal (step 910), or any other kind of variation expected to produce a VEP. As described above, these may be shown at different frequencies, which may or may not be harmonic. These patters may also, or alternatively, be shown at different phases. Again, to isolate the magnocellular and parvocellular pathways, and in recognition of the distribution of rods and cones in the eye, patterns near to the fovea may be reversed at a greater frequency that patterns far from the fovea (optional step 912).

To prevent a subject from intentionally or inadvertently looking directly at a single pattern, a letter, number, shape, or symbol may be shown at a region of the display to which foveation is targeted, and the subject may be asked simply to view this letter, number, shape, or symbol, or may be given a task, such as to respond to the presence of a particular letter, number, shape, or symbol (optional step 920). This step will be described in detail below, with reference to FIGS. 10a-10d.

As patterns are shown to the subject, the electrical activity of the brain is captured (step 930) and preferably recorded (optional step 940). Acquisition, sampling, and recording may all be performed in analog or preferably digital forms.

The above steps may be repeated until every region for which testing is desired has been properly stimulated, and then analysis may be performed on the acquired/recorded brainwaves. Alternatively, the above steps may be performed for a limited number of regions, analysis may then be performed on those regions, and then the above steps may be performed on different regions, with analysis then performed on those regions. Alternative to both of these, analysis may occur during the acquisition itself, thereby informing the operator immediately of any concerns, errors, or apparent deficits.

Thus, at some point, frequency components are resolved from the brain activity (step 950). As noted above, these may be resolved through the use of a Fourier transform (optional step 952), or another method. These resolved frequency components may be stored separately, or may be reduced to average values of magnitude and/or phase over periods of time. Optionally, frequency components corresponding to alpha or beta waves may also be resolved (optional step 960) and may be subtracted, or may be used as an indicator of subject attention.

Then, as described above, the resolved frequency components, each of which corresponding to a stimulated region of the visual field, may be used to determine the likelihood of any visual deficit (step 970). Their magnitudes may be compared (optional step 971). Their phases may be compared to the phases of the patterns as displayed (optional step 972). The magnitude of each frequency component may be individually determined (optional step 973) for comparison to a threshold value or for any other use. Summed magnitudes of subsets of frequency components may be compared (optional step 974). Comparisons may be made across different regions, or across the two eyes (optional step 975). Confidence intervals may be determined for each comparison (optional step 976). Other comparisons may also be used to determine the likelihood of a deficit.

Instructions for performing any or all of the above steps may be stored on a machine readable medium and operated by a computer.

Figure 10B:
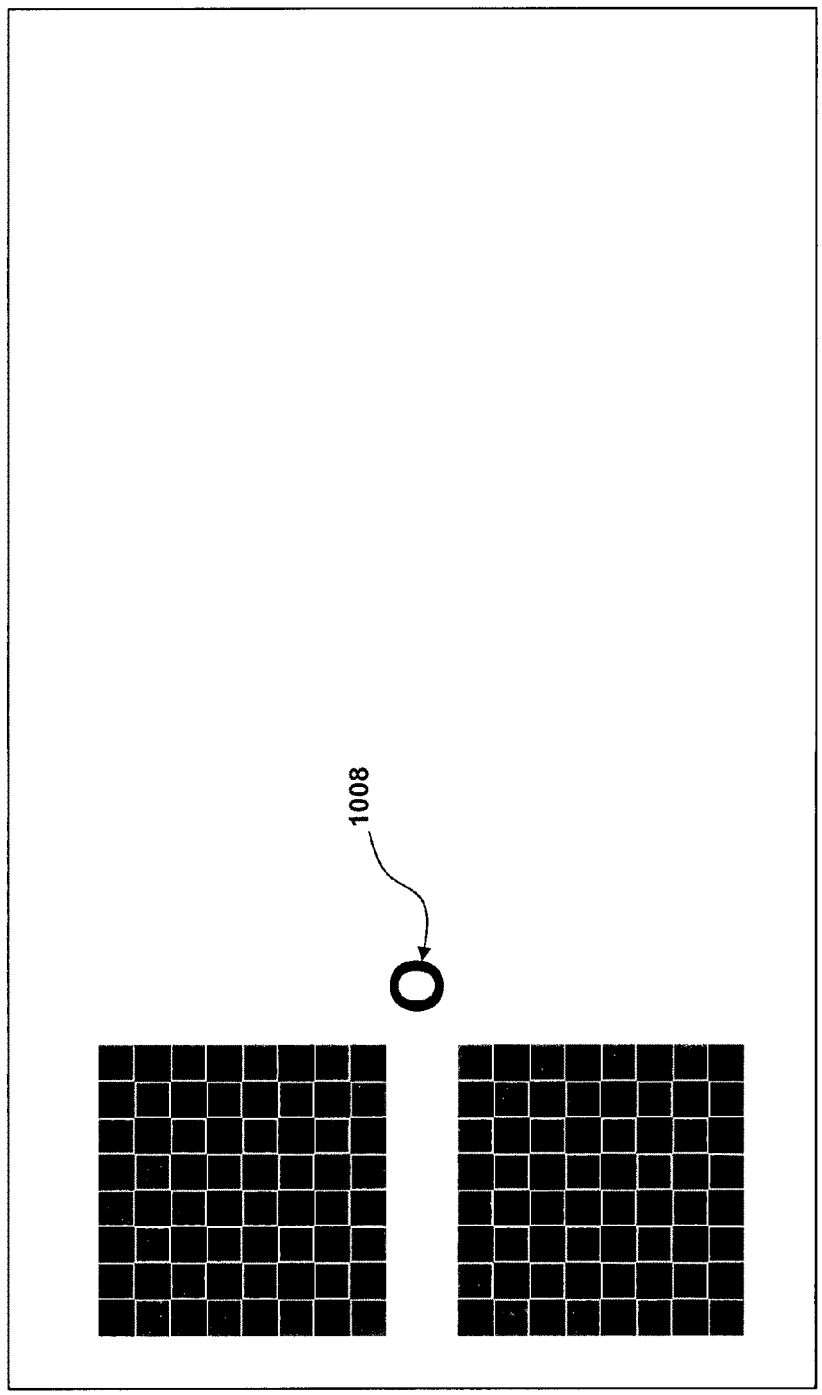
Figure 10C:
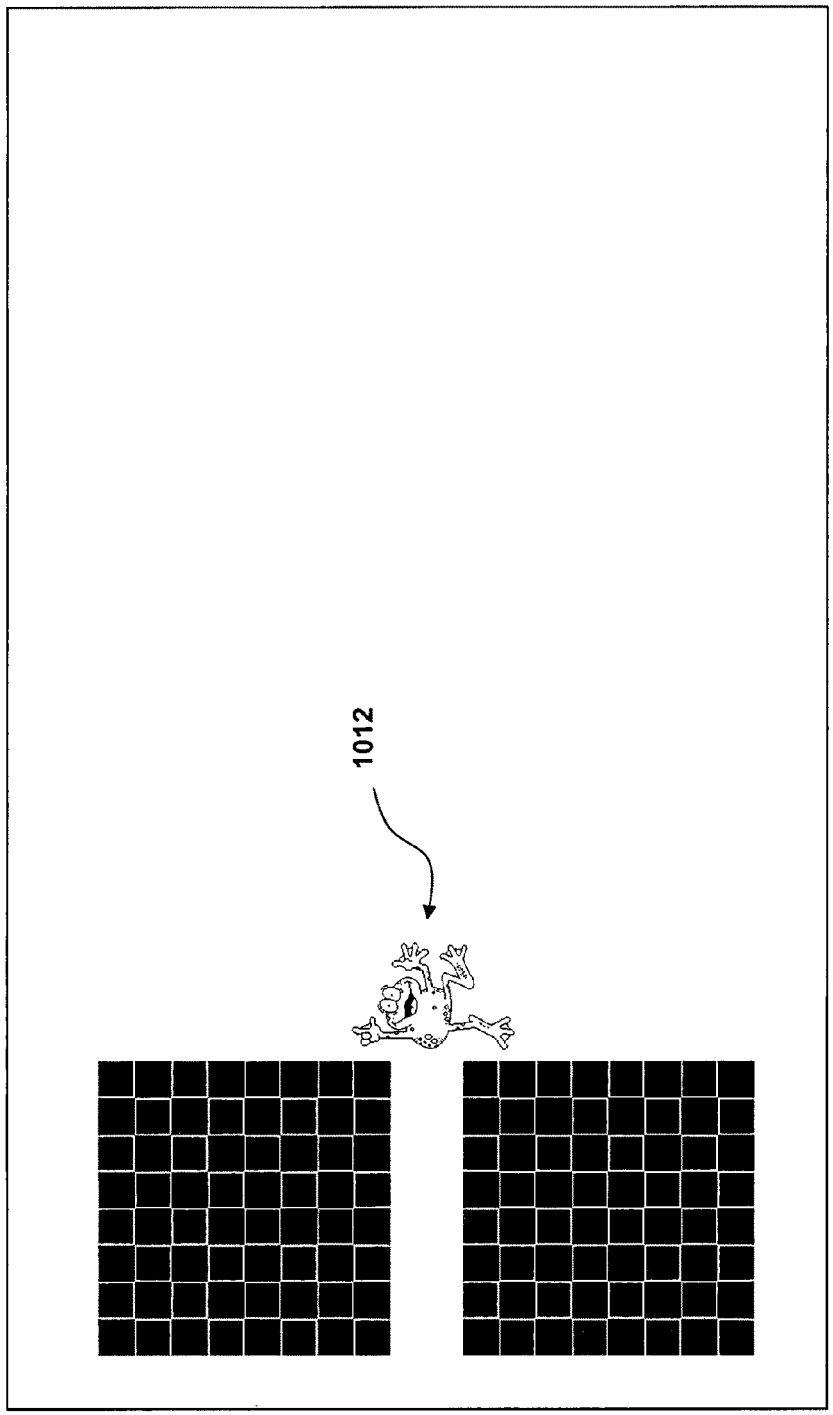
Figure 10D:
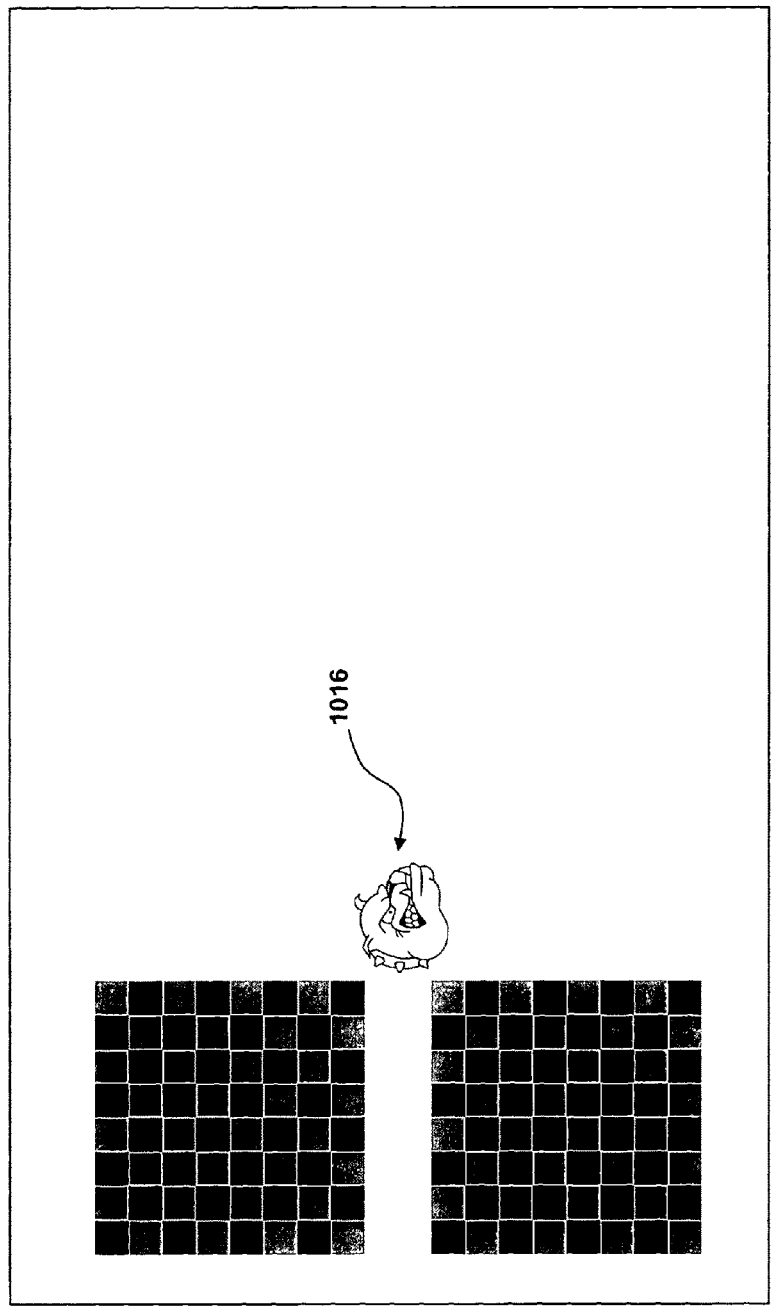

As noted above, it may be advantageous to encourage the subject to fixate on a particular regions of the display, to assure that the contrast-reversing patterns on the screen are shown to a particular region of the subject's visual field relative to the fovea. Accordingly, FIGS. 10*a*-10*d* illustrate one behavioral task which may be used to encourage the subject to attend to one area of the screen. As shown in FIG. 10*a*, the region 1000 is identified as the target of foveation, and the subject is instructed to watch this region, in which letters or symbols are displayed while the contrast reversals occur. For example, the subject may be asked to press a button whenever the letter O 1008 is shown. Thus, the subject merely attends to region 1000 while the letter X 1004 is observed, but as in FIG. 10*b* presses the button whenever the letter O 1008 is shown. If the subject is young or illiterate, symbols may be used instead, and the subject may, as in FIG. 10*c*, simply attend to the image of a frog 1012 shown in region 1000, but as in FIG. 10*d* may press the button whenever the image of a dog 1016 is shown.

While such behavioral tests are useful in assuring that the subject's vision remains directed to the desired location, it should be noted that the visualization of letters or pictures, or the identification of an expected or unexpected stimulus, may cause additional neural activity and evoked potentials (such as P300s and N400s) which must be accounted for in the data. Accordingly, along with recording the brain activity, the method may optionally include a record of any focus or behavioral stimulus shown to the subject, and when these stimuli were shown.

The previous description of some aspects is provided to enable any person skilled in the art to make or use the present invention. Various modifications to these aspects will be readily apparent to those skilled in the art, and the generic principles defined herein may be applied to other aspects without departing from the spirit or scope of the invention. For example, one or more elements can be rearranged and/or combined, or additional elements may be added. Thus, the present invention is not intended to be limited to the aspects shown herein but is to be accorded the widest scope consistent with the principles and novel features disclosed herein.

What is claimed is:

1. A method for determining a likelihood of a visual deficit in a subject by way of a simultaneously multi-temporal visual test, the method comprising:
   a. simultaneously displaying at least two visual patterns to a first eye of a subject, each pattern reversing in contrast or color at a different one of a corresponding number of display frequencies, a first of said patterns displayed to a first region of the subject's visual field and a second of said patterns displayed to a second region of a subject's visual field;
   b. sampling electrical activity of the brain of the subject to produce a first signal corresponding to the first pattern and a second signal corresponding to the second pattern;
   c. resolving one or more frequency components from each of said first signal and said second signal;
   d. repeating steps a-c for the second eye of a subject where a first and second visual field region of the second eye correspond to the first and second visual field region of the first eye;
   e. comparing at least one frequency component from a first or second signal in a first eye to at least one frequency component from a respective first or second signal in a second eye; and
   d. determining from one or more of the comparisons a measurement of a likelihood that a visual deficit exists in a visual area being tested.

2. The method of claim 1, wherein the determining step comprises comparing a magnitude measurement of one of the frequency components of a first eye to the magnitude measurement of a frequency component of the second eye.

3. The method of claim 1, wherein the determining step comprises comparing the phase of each frequency component to the phase of the corresponding visual pattern display.

4. The method of claim 3, wherein the determining step further comprises taking a magnitude measurement for each frequency component.

5. The method of claim 1, the method comprising:
   resolving from the signals each frequency component corresponding to each of the display frequencies; and
   wherein the determining step comprises comparing a summed magnitude of a first subset of the frequency components to a summed magnitude of a second subset of the frequency components.

6. The method of claim 5, wherein the first subset comprises frequency components corresponding to display frequencies displayed in the superior half of the subject's visual field, and the second subset comprises frequency components corresponding to display frequencies displayed in the inferior half of the subject's visual field.

7. The method of claim 5, wherein the first subset comprises frequency components corresponding to display frequencies displayed in a nasal portion of the subject's visual field, and the second subset comprises frequency components corresponding to display frequencies displayed in a temporal portion of the subject's visual field.

8. The method of claim 1, wherein the displaying step comprises simultaneously displaying up to eight visual patterns to one eye of the subject, each pattern reversing in contrast or color at a different display frequency, each of the visual patterns reversing in contrast or color at a different display phase, wherein half of the visual patterns is displayed to the superior half of subject's visual field and the other half of the visual patterns is displayed to the inferior half of subject's visual field.

9. The method of claim 1, wherein the displaying step comprises:
   displaying visual patterns with low contrast horizontally displaced from the subject's fovea at an observation angle of over 5 degrees; and
   displaying visual patterns with high contrast horizontally displaced from the subject's fovea at an observation angle between 1.5 degrees and 5 degrees.

10. The method of claim 9, wherein the displaying step further comprises:
    displaying visual patterns with low contrast horizontally displaced from the subject's fovea at an observation angle between 1.5 degrees and 5 degrees; and
    displaying visual patterns with high contrast horizontally displaced from the subject's fovea at an observation angle of over 5 degrees.

11. The method of claim 1, wherein the displaying step comprises:
    displaying visual patterns comprising checkerboard patterns of a first grid size horizontally displaced from the subject's fovea at an observation angle between 1.5 degrees and 5 degrees; and displaying visual patterns comprising checkerboard patterns of a second grid size horizontally displaced from the subject's fovea at an observation angle of over 5 degrees.

12. The method of claim 1, wherein the displaying step comprises:
    displaying visual patterns comprising checkerboard patterns horizontally is placed from the subject's fovea at an observation angle between 1.5 degrees and 5 degrees; and
    displaying visual patterns comprising checkerboard patterns horizontally displaced from the subject's fovea at an observation angle of over 5 degrees, wherein each checkerboard patterns displayed between 1.5 degrees and 5 degrees displaced from subject's fovea reverses in contrast at a display frequency greater than the largest display frequency at which a checkerboard pattern displayed over 5 degrees displaced from subject's fovea reverses in contrast.

13. The method of claim 1, the method further comprising:
    displaying a letter, number, shape, or symbol at a location to which the subject's vision is directed; and instructing the subject to identify an occurrence of the display of at least one particular letter, number, shape, or symbol, thereby assuring that the subject's vision remains directed to said location.

14. The method of claim 1, the method further comprising:
    resolving a further frequency component from the signal corresponding to at least one likely alpha or beta wave; and subtracting the alpha or beta frequency component from the signal prior to the determining step.

15. The method of claim 1, wherein the displaying step is performed at least once for the subject's first eye and at least once for the subject's second eye, the patterns for the first eye and the patterns for the second eye shown to mirror-isometric regions of the first and second eyes' respective visual fields, and wherein the determining step comprises comparing the magnitude of one of the frequency components resolved from the testing of one eye to the magnitude of a corresponding one of the frequency components resolved from the testing of the other eye.

16. The method of claim 1, wherein the resolving step comprises resolving the one or more frequency components by way of a Fourier transform.

17. The method of claim 1, wherein the electrical activity is captured at a scalp region directly above the visual cortex of the brain.

18. The method of claim 1, the method further comprising:
    recording the signal; and determining confidence intervals for the frequency components by use of $T^2_{circ}$ statistics.

19. The method of claim 1, wherein the visual deficit signifies the presence of at least one selected from the group consisting of: glaucoma; macular degeneration; macular dystrophy; retinitis pigmentosa; Laurence-Moon-Bardet-Biedl syndrome; Stargardt's disease; inflammation of the retina; inflammation of the choroid; Serpiginous Choroiditis; cortical blindness; cataracts; basic refractive problems; strabismus; and combinations thereof.

20. A machine readable medium comprising instructions for performing the method of claim 1.

21. A method for determining a likelihood of a visual deficit in a subject by way of a simultaneously multi-temporal visual test, the method comprising:
    a. simultaneously displaying at least two visual patterns to an eye of a subject, each pattern reversing in contrast or color at a different one of a corresponding number of display frequencies, a first of said patterns displayed to a first region of the subject's visual field and a second of said patterns displayed to a second region of a subject's visual field;
    b. sampling electrical activity of the brain of the subject to produce a first signal corresponding to the first pattern and a second signal corresponding to the second pattern;
    c. resolving one or more frequency components from each of said first signal and said second signal said frequency component comprising at least one of magnitude and phase;
    d. comparing at least one frequency component from a first visual field region to at least one frequency component from a second visual field region of said eye; and
    e. determining from one or more of the comaprisons a measurement of a likelihood that a visual deficit exists in a visual being tested.

22. A method for determining a likelihood of a visual deficit in a subject by way of a simultaneously multi-temporal visual test, the method comprising:
    a. simultaneously displaying a plurality of visual patterns to a first eye of a subject, each pattern reversing in contrast or color at a different one of a corresponding number of display frequencies;
    b. sampling electrical activity of the brain of the subject to produce a plurality of signals corresponding to plurality of visual patterns displayed to said first eye;
    c. resolving at least one parameter of said signals corresponding to said plurality of visual patterns;
    d. summing a subset of said parameters resolved in step c., said subset corresponding to a region of a visual field;
    e. repeating steps a-d for the second eye of a subject;
    f. comparing summed parameters of a subset of a first eye to summed parameters of a subset of a second eye; and g. determining from said comparison a measurement of a likelihood that a visual deficit exists in a visual area corresponding to one of said subsets.

23. A method for determining a likelihood of a visual deficit in a subject by way of a simultaneously multi-temporal visual test, the method comprising:
   a. simultaneously displaying a plurality of visual patterns to a first eye of a subject, each pattern reversing in contrast or color at a different one of a corresponding number of display frequencies;
   b. sampling electrical activity of the brain of the subject to produce a plurality of signals corresponding to plurality of visual patterns displayed to said first eye;
   c. resolving the magnitudes of said signals corresponding to said plurality of visual patterns;
   d. summing the magnitudes of a subset of said magnitudes resolved in step c., said subset corresponding to a region of a visual field;
   e. repeating steps a-d for the second eye of a subject;
   f. comparing summed magnitudes of a subset of a first eye to summed magnitudes of a subset of a second eye; and
   g. determining from said comparison a measurement of a likelihood that a visual deficit exists in a visual area corresponding to one of said subsets.

* * * * *